(12) United States Patent
Mei et al.

(10) Patent No.: US 12,178,444 B2
(45) Date of Patent: Dec. 31, 2024

(54) CLIP REMOVAL SYSTEMS AND METHODS

(71) Applicant: Evalve, Inc., Santa Clara, CA (US)

(72) Inventors: Shengmin Mei, Fremont, CA (US);
Gabriel R. Gonzales, Milpitas, CA (US); Alexander Chu, Diamond Bar, CA (US); Richard Thomas Childs, San Francisco, CA (US)

(73) Assignee: Evalve, Inc., Santa Clara, CA (US)

(*) Notice: Subject to any disclaimer, the term of this patent is extended or adjusted under 35 U.S.C. 154(b) by 104 days.

(21) Appl. No.: 17/306,407

(22) Filed: May 3, 2021

(65) Prior Publication Data

US 2021/0346029 A1 Nov. 11, 2021

Related U.S. Application Data

(60) Provisional application No. 63/020,673, filed on May 6, 2020.

(51) Int. Cl.
*A61B 17/128* (2006.01)
*A61B 17/32* (2006.01)
(Continued)

(52) U.S. Cl.
CPC ...... *A61B 17/1285* (2013.01); *A61B 17/3205* (2013.01); *A61B 18/1492* (2013.01);
(Continued)

(58) Field of Classification Search
CPC ............ A61B 17/1285; A61B 17/3205; A61B 18/1492; A61B 2017/320052;
(Continued)

(56) References Cited

U.S. PATENT DOCUMENTS 1,996,261 A 4/1935 Storz
2,097,018 A 10/1937 Chamberlin
(Continued)

FOREIGN PATENT DOCUMENTS

CN 1469724 A 1/2004
CN 102770080 A 11/2012
(Continued)

OTHER PUBLICATIONS

Nishimura, et al. 2014 AHA/ACC guideline for the management of patients with valvular heart disease: executive summary: a report of the American College of Cardiology/American Heart Association Task Force on Practice Guidelines. J Am Coll Cardiol. Jun. 10, 2014; 63(22):2438-88.
(Continued)

*Primary Examiner* — Linda C Dvorak
*Assistant Examiner* — Abigail Bock
(74) *Attorney, Agent, or Firm* — Workman Nydegger

(57) ABSTRACT

A system configured to detach an interventional implant from a cardiac valve includes a guide catheter and a capture mechanism routable through the guide catheter. The capture mechanism comprises a capture hypotube with a container portion/space configured to receive an interventional implant connected to cardiac valve tissue. The capture mechanism also includes a cutting arm axially moveable relative to the capture hypotube. The capture hypotube and the cutting arm each include cutting elements that are brought together upon actuation of the cutting arm to thereby cut the cardiac valve tissue surrounding the interventional implant to free the implant from the cardiac valve.

19 Claims, 8 Drawing Sheets

(51) Int. Cl.
    *A61B 17/3205*     (2006.01)
    *A61B 18/00*     (2006.01)
    *A61B 18/14*     (2006.01)
    *A61M 25/01*     (2006.01)

(52) U.S. Cl.
    CPC .......... *A61M 25/0136* (2013.01); *A61B 2017/320052* (2013.01); *A61B 2018/00083* (2013.01); *A61B 2018/00369* (2013.01); *A61B 2018/00601* (2013.01); *A61B 2018/1422* (2013.01); *A61M 25/0147* (2013.01)

(58) Field of Classification Search
    CPC   A61B 2018/00083; A61B 2018/00369; A61B 2018/00601; A61B 2018/1422; A61B 17/0467; A61B 17/32; A61B 2017/320012; A61B 2017/320733; A61M 25/0136; A61M 25/0147
    See application file for complete search history.

(56) References Cited

U.S. PATENT DOCUMENTS

| | | |
|---|---|---|
| 2,108,206 A | 2/1938 | Mecker |
| 3,296,668 A | 1/1967 | Aiken |
| 3,378,010 A | 4/1968 | Codling et al. |
| 3,470,875 A | 10/1969 | Johnson |
| 3,557,780 A | 1/1971 | Sato |
| 3,671,979 A | 6/1972 | Moulopoulos |
| 3,675,639 A | 7/1972 | Cimber |
| 3,776,237 A | 12/1973 | Hill et al. |
| 3,874,338 A | 4/1975 | Happel |
| 3,874,388 A | 4/1975 | King et al. |
| 4,007,743 A | 2/1977 | Blake |
| 4,056,854 A | 11/1977 | Boretos et al. |
| 4,064,881 A | 12/1977 | Meredith |
| 4,091,815 A | 5/1978 | Larsen |
| 4,112,951 A | 9/1978 | Hulka et al. |
| 4,235,238 A | 11/1980 | Ogiu et al. |
| 4,297,749 A | 11/1981 | Davis et al. |
| 4,312,337 A | 1/1982 | Donohue |
| 4,425,908 A | 1/1984 | Simon |
| 4,458,682 A | 7/1984 | Cerwin |
| 4,484,579 A | 11/1984 | Meno et al. |
| 4,487,205 A | 12/1984 | Di et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,686,965 A | 8/1987 | Bonnet et al. |
| 4,777,951 A | 10/1988 | Cribier et al. |
| 4,809,695 A | 3/1989 | Gwathmey et al. |
| 4,872,455 A | 10/1989 | Pinchuk et al. |
| 4,878,495 A | 11/1989 | Grayzel |
| 4,917,089 A | 4/1990 | Sideris |
| 4,944,295 A | 7/1990 | Gwathmey et al. |
| 4,969,890 A | 11/1990 | Sugita et al. |
| 4,994,077 A | 2/1991 | Dobben |
| 5,015,249 A | 5/1991 | Nakao et al. |
| 5,019,096 A | 5/1991 | Fox et al. |
| 5,042,707 A | 8/1991 | Taheri |
| 5,047,041 A | 9/1991 | Samuels |
| 5,049,153 A | 9/1991 | Nakao et al. |
| 5,053,043 A | 10/1991 | Gottesman et al. |
| 5,061,277 A | 10/1991 | Carpentier et al. |
| 5,069,679 A | 12/1991 | Taheri |
| 5,071,428 A | 12/1991 | Chin et al. |
| 5,078,722 A | 1/1992 | Stevens |
| 5,078,723 A | 1/1992 | Dance et al. |
| 5,108,368 A | 4/1992 | Hammerslag et al. |
| 5,125,758 A | 6/1992 | Dewan |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,217,460 A | 6/1993 | Knoepfler |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,330,442 A | 7/1994 | Green et al. |
| 5,332,402 A | 7/1994 | Teitelbaum |
| 5,336,227 A | 8/1994 | Nakao et al. |
| 5,342,393 A | 8/1994 | Stack |
| 5,350,397 A | 9/1994 | Palermo et al. |
| 5,350,399 A | 9/1994 | Erlebacher et al. |
| 5,359,994 A | 11/1994 | Krauter et al. |
| 5,368,564 A | 11/1994 | Savage |
| 5,368,601 A | 11/1994 | Sauer et al. |
| 5,373,854 A | 12/1994 | Kolozsi |
| 5,383,886 A | 1/1995 | Kensey et al. |
| 5,387,219 A | 2/1995 | Rappe |
| 5,391,182 A | 2/1995 | Chin |
| 5,395,030 A | 3/1995 | Kuramoto et al. |
| 5,403,312 A | 4/1995 | Yates et al. |
| 5,403,326 A | 4/1995 | Harrison et al. |
| 5,411,552 A | 5/1995 | Andersen et al. |
| 5,417,684 A | 5/1995 | Jackson et al. |
| 5,417,699 A | 5/1995 | Klein et al. |
| 5,417,700 A | 5/1995 | Egan |
| 5,423,830 A | 6/1995 | Schneebaum et al. |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,472,423 A | 12/1995 | Gronauer |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,496,332 A | 3/1996 | Sierra et al. |
| 5,507,725 A | 4/1996 | Savage et al. |
| 5,507,755 A | 4/1996 | Gresl et al. |
| 5,507,757 A | 4/1996 | Sauer et al. |
| 5,520,701 A | 5/1996 | Karl-Dieter |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,562,678 A | 10/1996 | Booker |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |

(56) References Cited

U.S. PATENT DOCUMENTS

| | | |
|---|---|---|
| 5,575,802 A | 11/1996 | McQuilkin et al. |
| 5,582,611 A | 12/1996 | Tsuruta et al. |
| 5,584,803 A | 12/1996 | Stevens et al. |
| 5,593,424 A | 1/1997 | Northrup III |
| 5,593,435 A | 1/1997 | Carpentier et al. |
| 5,609,598 A | 3/1997 | Laufer et al. |
| 5,617,854 A | 4/1997 | Munsif |
| 5,618,306 A | 4/1997 | Roth et al. |
| 5,620,452 A | 4/1997 | Yoon |
| 5,620,461 A | 4/1997 | Muijs et al. |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 5,669,919 A | 9/1997 | Sanders et al. |
| 5,690,671 A | 11/1997 | McGurk et al. |
| 5,695,504 A | 12/1997 | Gifford et al. |
| 5,695,505 A | 12/1997 | Yoon |
| 5,702,825 A | 12/1997 | Keita et al. |
| 5,706,824 A | 1/1998 | Whittier |
| 5,709,707 A | 1/1998 | Ock et al. |
| 5,713,910 A | 2/1998 | Gordon et al. |
| 5,713,911 A | 2/1998 | Racenet et al. |
| 5,715,817 A | 2/1998 | Stevens-Wright et al. |
| 5,716,367 A | 2/1998 | Koike et al. |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,271 A | 4/1998 | Nakao et al. |
| 5,741,280 A | 4/1998 | Fleenor |
| 5,746,747 A | 5/1998 | McKeating |
| 5,749,828 A | 5/1998 | Yeung |
| 5,759,193 A | 6/1998 | Burbank et al. |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,591 A | 10/1998 | Thompson et al. |
| 5,820,592 A | 10/1998 | Hammerslag |
| 5,820,630 A | 10/1998 | Lind |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,843,103 A | 12/1998 | Wulfman |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,855,614 A | 1/1999 | Stevens et al. |
| 5,860,990 A | 1/1999 | Nobles et al. |
| 5,861,003 A | 1/1999 | Atson et al. |
| 5,868,733 A | 2/1999 | Ockuly et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson et al. |
| 5,895,404 A | 4/1999 | Ruiz |
| 5,895,417 A | 4/1999 | Pomeranz et al. |
| 5,906,620 A | 5/1999 | Nakao et al. |
| 5,908,420 A | 6/1999 | Parins et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhardt et al. |
| 5,957,973 A | 9/1999 | Quiachon et al. |
| 5,972,020 A | 10/1999 | Carpentier et al. |
| 5,972,030 A | 10/1999 | Garrison et al. |
| 5,980,455 A | 11/1999 | Daniel et al. |
| 5,989,284 A | 11/1999 | Laufer |
| 5,997,547 A | 12/1999 | Nakao et al. |
| 6,007,546 A | 12/1999 | Snow et al. |
| 6,015,417 A | 1/2000 | Reynolds, Jr. |
| 6,019,722 A | 2/2000 | Spence et al. |
| 6,022,360 A | 2/2000 | Reimels et al. |
| 6,033,378 A | 3/2000 | Lundquist et al. |
| 6,033,419 A | 3/2000 | Hamblin et al. |
| 6,036,699 A | 3/2000 | Andreas et al. |
| 6,048,351 A | 4/2000 | Gordon et al. |
| 6,053,933 A | 4/2000 | Balazs et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,086,600 A | 7/2000 | Kortenbach |
| 6,088,889 A | 7/2000 | Luther et al. |
| 6,090,118 A | 7/2000 | McGuckin, Jr. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,123,665 A | 9/2000 | Kawano |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,139,508 A | 10/2000 | Simpson et al. |
| 6,143,024 A | 11/2000 | Campbell et al. |
| 6,159,240 A | 12/2000 | Sparer et al. |
| 6,162,233 A | 12/2000 | Williamson et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,174,322 B1 | 1/2001 | Schneidt |
| 6,180,059 B1 | 1/2001 | Divino et al. |
| 6,182,664 B1 | 2/2001 | Cosgrove |
| 6,187,003 B1 | 2/2001 | Buysse et al. |
| 6,190,408 B1 | 2/2001 | Melvin |
| 6,197,043 B1 | 3/2001 | Davidson |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,245,079 B1 | 6/2001 | Nobles et al. |
| 6,264,617 B1 | 7/2001 | Bales et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |

(56) References Cited

U.S. PATENT DOCUMENTS

| | | |
|---|---|---|
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,334,860 B1 | 1/2002 | Dorn |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley et al. |
| 6,402,780 B2 | 6/2002 | Williamson et al. |
| 6,402,781 B1 | 6/2002 | Angberg et al. |
| 6,406,420 B1 | 6/2002 | McCarthy et al. |
| 6,419,640 B1 | 7/2002 | Taylor |
| 6,419,669 B1 | 7/2002 | Frazier et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,508,828 B1 | 1/2003 | Akerfeldt et al. |
| 6,517,550 B1 | 2/2003 | Konya et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,921 B2 | 9/2003 | Blatter et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Horner |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,932,810 B2 | 8/2005 | Ryan |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen et al. |
| 7,011,669 B2 | 3/2006 | Kimblad |
| 7,033,390 B2 | 4/2006 | Johnson et al. |
| 7,048,754 B2 | 5/2006 | Martin et al. |
| 7,056,294 B2 | 6/2006 | Khairkhahan et al. |
| 7,112,207 B2 | 9/2006 | Allen et al. |
| 7,226,467 B2 | 6/2007 | Lucatero et al. |
| 7,258,694 B1 | 8/2007 | Choi et al. |
| 7,288,097 B2 | 10/2007 | Seguin |
| 7,291,168 B2 | 11/2007 | Macoviak et al. |
| 7,338,467 B2 | 3/2008 | Lutter |
| 7,381,210 B2 | 6/2008 | Zarbatany et al. |
| 7,435,257 B2 | 10/2008 | Lashinski et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 7,666,204 B2 | 2/2010 | Thornton et al. |
| 7,955,340 B2 | 6/2011 | Michlitsch et al. |
| 8,216,234 B2 | 7/2012 | Long |
| 8,257,356 B2 | 9/2012 | Bleich et al. |
| 8,398,708 B2 | 3/2013 | Meiri et al. |
| 8,435,237 B2 | 5/2013 | Bahney |
| 8,496,655 B2 | 7/2013 | Epp et al. |
| 8,500,768 B2 | 8/2013 | Cohen |
| 8,523,881 B2 | 9/2013 | Cabiri et al. |
| 8,623,077 B2 | 1/2014 | Cohn |
| 8,690,858 B2 | 4/2014 | Machold et al. |
| 8,821,518 B2 | 9/2014 | Saliman et al. |
| 8,926,588 B2 | 1/2015 | Berthiaume et al. |
| 9,126,032 B2 | 9/2015 | Khairkhahan et al. |
| 9,211,119 B2 | 12/2015 | Hendricksen et al. |
| 9,370,341 B2 | 6/2016 | Ceniccola et al. |
| 9,498,331 B2 | 11/2016 | Chang et al. |
| 9,572,666 B2 | 2/2017 | Basude et al. |
| 9,770,256 B2 | 9/2017 | Cohen et al. |
| 9,949,833 B2 | 4/2018 | McCleary et al. |
| 10,238,493 B1 | 3/2019 | Metchik et al. |
| 10,667,804 B2 | 6/2020 | Basude et al. |
| 11,013,554 B2 | 5/2021 | Coates |
| 11,406,250 B2 | 8/2022 | Saadat et al. |
| 2001/0002445 A1 | 5/2001 | Vesely |
| 2001/0004715 A1 | 6/2001 | Duran et al. |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Angberg et al. |
| 2001/0044635 A1 | 11/2001 | Niizeki et al. |
| 2002/0013547 A1 | 1/2002 | Paskar |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Angberg et al. |
| 2002/0107534 A1 | 8/2002 | Schaefer et al. |
| 2002/0147456 A1 | 10/2002 | Diduch et al. |
| 2002/0156526 A1 | 10/2002 | Hlavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0173811 A1 | 11/2002 | Tu et al. |
| 2002/0173841 A1 | 11/2002 | Ortiz et al. |
| 2002/0183766 A1 | 12/2002 | Seguin |
| 2002/0183787 A1 | 12/2002 | Wahr et al. |
| 2002/0183835 A1 | 12/2002 | Taylor et al. |

(56) References Cited

U.S. PATENT DOCUMENTS

| | | |
|---|---|---|
| 2003/0005797 A1 | 1/2003 | Hopper et al. |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0015232 A1 | 1/2004 | Shu et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030319 A1 | 2/2004 | Korkor et al. |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0059345 A1 | 3/2004 | Nakao et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092858 A1 | 5/2004 | Wilson et al. |
| 2004/0092962 A1 | 5/2004 | Thornton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0116848 A1 | 6/2004 | Gardeski et al. |
| 2004/0116951 A1 | 6/2004 | Rosengart |
| 2004/0122448 A1 | 6/2004 | Levine |
| 2004/0127849 A1 | 7/2004 | Kantor |
| 2004/0127981 A1 | 7/2004 | Rahdert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133232 A1 | 7/2004 | Rosenbluth et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0147826 A1 | 7/2004 | Peterson |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Liska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225233 A1 | 11/2004 | Frankowski et al. |
| 2004/0225300 A1 | 11/2004 | Goldfarb et al. |
| 2004/0225305 A1 | 11/2004 | Ewers et al. |
| 2004/0225353 A1 | 11/2004 | McGuckin et al. |
| 2004/0236354 A1 | 11/2004 | Seguin |
| 2004/0242960 A1 | 12/2004 | Orban |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Rahdert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goar et al. |
| 2005/0021057 A1 | 1/2005 | St. Goar et al. |
| 2005/0021058 A1 | 1/2005 | Negro |
| 2005/0033446 A1 | 2/2005 | Deem et al. |
| 2005/0038383 A1 | 2/2005 | Kelley et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0065453 A1 | 3/2005 | Shabaz et al. |
| 2005/0085903 A1 | 4/2005 | Jan |
| 2005/0119735 A1 | 6/2005 | Spence et al. |
| 2005/0131438 A1 | 6/2005 | Cohn |
| 2005/0143809 A1 | 6/2005 | Salahieh et al. |
| 2005/0149014 A1 | 7/2005 | Hauck et al. |
| 2005/0159763 A1 | 7/2005 | Mollenauer et al. |
| 2005/0159810 A1 | 7/2005 | Filsoufi |
| 2005/0192633 A1 | 9/2005 | Montpetit |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0256452 A1 | 11/2005 | Demarchi et al. |
| 2005/0267493 A1 | 12/2005 | Schreck et al. |
| 2005/0273160 A1 | 12/2005 | Lashinski et al. |
| 2005/0277876 A1 | 12/2005 | Hayden |
| 2005/0287493 A1 | 12/2005 | Novak et al. |
| 2006/0004247 A1 | 1/2006 | Kute et al. |
| 2006/0009759 A1 | 1/2006 | Chrisitian |
| 2006/0015003 A1 | 1/2006 | Moaddes et al. |
| 2006/0015179 A1 | 1/2006 | Bulman-Fleming et al. |
| 2006/0020275 A1 | 1/2006 | Goldfarb et al. |
| 2006/0020327 A1 | 1/2006 | Lashinski et al. |
| 2006/0020334 A1* | 1/2006 | Lashinski ............... A61F 2/014 623/2.11 |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0074484 A1 | 4/2006 | Huber |
| 2006/0089671 A1 | 4/2006 | Goldfarb et al. |
| 2006/0089711 A1 | 4/2006 | Dolan |
| 2006/0135961 A1 | 6/2006 | Rosenman et al. |
| 2006/0135993 A1 | 6/2006 | Seguin |
| 2006/0184198 A1 | 8/2006 | Bales et al. |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Rahdert et al. |
| 2006/0276890 A1 | 12/2006 | Solem et al. |
| 2007/0016225 A1 | 1/2007 | Nakao |
| 2007/0038293 A1 | 2/2007 | St.Goar et al. |
| 2007/0060997 A1 | 3/2007 | De Boer |
| 2007/0073185 A1 | 3/2007 | Nakao |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |

(56) References Cited

U.S. PATENT DOCUMENTS

| | | |
|---|---|---|
| 2007/0173757 A1 | 7/2007 | Levine et al. |
| 2007/0197858 A1 | 8/2007 | Goldfarb et al. |
| 2007/0198082 A1 | 8/2007 | Kapadia et al. |
| 2007/0260225 A1 | 11/2007 | Sakakine et al. |
| 2007/0287884 A1 | 12/2007 | Schena |
| 2008/0009858 A1 | 1/2008 | Rizvi |
| 2008/0039935 A1 | 2/2008 | Buch et al. |
| 2008/0045936 A1 | 2/2008 | Vaska et al. |
| 2008/0051703 A1 | 2/2008 | Thornton et al. |
| 2008/0051807 A1 | 2/2008 | St. Goar et al. |
| 2008/0097467 A1 | 4/2008 | Gruber et al. |
| 2008/0097489 A1 | 4/2008 | Goldfarb et al. |
| 2008/0167714 A1 | 7/2008 | St. Goar et al. |
| 2008/0183194 A1 | 7/2008 | Goldfarb et al. |
| 2008/0188850 A1 | 8/2008 | Mody et al. |
| 2008/0195126 A1 | 8/2008 | Solem |
| 2008/0243249 A1 | 10/2008 | Kohm et al. |
| 2008/0294175 A1 | 11/2008 | Bardsley et al. |
| 2008/0312496 A1 | 12/2008 | Zwolinski |
| 2009/0012538 A1 | 1/2009 | Saliman et al. |
| 2009/0036768 A1 | 2/2009 | Seehusen et al. |
| 2009/0156995 A1 | 6/2009 | Martin et al. |
| 2009/0163934 A1 | 6/2009 | Raschdorf et al. |
| 2009/0177266 A1 | 7/2009 | Powell et al. |
| 2009/0192510 A1 | 7/2009 | Bahney |
| 2009/0198322 A1 | 8/2009 | Deem et al. |
| 2009/0204005 A1 | 8/2009 | Keast et al. |
| 2009/0209955 A1 | 8/2009 | Forster et al. |
| 2009/0209991 A1 | 8/2009 | Hinchliffe et al. |
| 2009/0270858 A1 | 10/2009 | Hauck et al. |
| 2009/0276039 A1 | 11/2009 | Meretei |
| 2009/0281619 A1 | 11/2009 | Le et al. |
| 2009/0326567 A1 | 12/2009 | Goldfarb et al. |
| 2010/0016958 A1 | 1/2010 | St. Goar et al. |
| 2010/0022823 A1 | 1/2010 | Goldfarb et al. |
| 2010/0044410 A1 | 2/2010 | Argentine et al. |
| 2010/0121437 A1 | 5/2010 | Subramanian et al. |
| 2010/0152612 A1 | 6/2010 | Headley et al. |
| 2010/0217261 A1 | 8/2010 | Watson |
| 2010/0262231 A1 | 10/2010 | Tuval et al. |
| 2010/0268226 A1 | 10/2010 | Epp et al. |
| 2010/0298929 A1 | 11/2010 | Thornton et al. |
| 2011/0009864 A1 | 1/2011 | Bucciaglia et al. |
| 2011/0184405 A1 | 7/2011 | Mueller |
| 2011/0224710 A1 | 9/2011 | Bleich |
| 2011/0238052 A1 | 9/2011 | Robinson |
| 2012/0022527 A1 | 1/2012 | Woodruff et al. |
| 2012/0022640 A1 | 1/2012 | Gross et al. |
| 2012/0065464 A1 | 3/2012 | Ellis et al. |
| 2012/0150194 A1 | 6/2012 | Odermatt et al. |
| 2012/0157765 A1 | 6/2012 | Mitelberg |
| 2012/0172915 A1 | 7/2012 | Fifer et al. |
| 2012/0179184 A1 | 7/2012 | Orlov |
| 2012/0265222 A1 | 10/2012 | Gordin et al. |
| 2012/0310330 A1 | 12/2012 | Buchbinder et al. |
| 2012/0316639 A1 | 12/2012 | Kleinschrodt |
| 2012/0330348 A1 | 12/2012 | Strauss et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0109910 A1 | 5/2013 | Alexander et al. |
| 2013/0172828 A1 | 7/2013 | Kappel et al. |
| 2013/0317515 A1 | 11/2013 | Kuroda et al. |
| 2014/0039511 A1 | 2/2014 | Morris et al. |
| 2014/0135799 A1 | 5/2014 | Henderson |
| 2014/0228871 A1 | 8/2014 | Cohen et al. |
| 2014/0276913 A1 | 9/2014 | Tah et al. |
| 2014/0309670 A1 | 10/2014 | Bakos et al. |
| 2014/0324164 A1 | 10/2014 | Gross et al. |
| 2014/0350662 A1 | 11/2014 | Vaturi |
| 2014/0358224 A1 | 12/2014 | Tegels et al. |
| 2014/0364866 A1 | 12/2014 | Dryden et al. |
| 2014/0379074 A1 | 12/2014 | Spence et al. |
| 2015/0005704 A1 | 1/2015 | Heisel et al. |
| 2015/0005801 A1 | 1/2015 | Marquis et al. |
| 2015/0051698 A1 | 2/2015 | Ruyra et al. |
| 2015/0094800 A1 | 4/2015 | Chawla |
| 2015/0112430 A1 | 4/2015 | Creaven et al. |
| 2015/0211946 A1 | 7/2015 | Pons et al. |
| 2015/0230947 A1 | 8/2015 | Krieger et al. |
| 2015/0257877 A1 | 9/2015 | Hernandez |
| 2015/0257883 A1* | 9/2015 | Basude ............ A61B 17/0682 623/2.11 |
| 2015/0306806 A1 | 10/2015 | Dando et al. |
| 2015/0313581 A1 | 11/2015 | Wolfe et al. |
| 2016/0015410 A1 | 1/2016 | Asirvatham et al. |
| 2016/0074165 A1 | 3/2016 | Spence et al. |
| 2016/0174979 A1 | 6/2016 | Wei |
| 2016/0317174 A1 | 11/2016 | Dake |
| 2017/0042678 A1 | 2/2017 | Ganesan et al. |
| 2017/0100183 A1 | 4/2017 | Iaizzo et al. |
| 2017/0143330 A1 | 5/2017 | Basude et al. |
| 2017/0202559 A1 | 7/2017 | Taha |
| 2017/0232238 A1 | 8/2017 | Biller et al. |
| 2018/0008268 A1 | 1/2018 | Khairkhahan |
| 2018/0028215 A1 | 2/2018 | Cohen |
| 2018/0092661 A1 | 4/2018 | Prabhu |
| 2018/0133010 A1 | 5/2018 | Kizuka |
| 2018/0161159 A1 | 6/2018 | Lee et al. |
| 2018/0360457 A1 | 12/2018 | Ellis et al. |
| 2019/0029790 A1 | 1/2019 | Bak-Boychuk et al. |
| 2019/0183571 A1 | 6/2019 | De Marchena |
| 2019/0298517 A1 | 10/2019 | Sanchez et al. |
| 2019/0307458 A1 | 10/2019 | Mathis et al. |
| 2020/0121460 A1 | 4/2020 | Dale et al. |
| 2021/0113232 A1* | 4/2021 | Ortiz Garcia ...... A61B 17/0467 |
| 2021/0145574 A1 | 5/2021 | Childs et al. |

FOREIGN PATENT DOCUMENTS

| | | | |
|---|---|---|---|
| CN | 103841899 A | 6/2014 | |
| CN | 104244841 A | 12/2014 | |
| DE | 3504292 C1 | 7/1986 | |
| DE | 9100873 U1 | 4/1991 | |
| DE | 10116168 A1 | 11/2001 | |
| EP | 0179562 A1 | 4/1986 | |
| EP | 0558031 A2 | 9/1993 | |
| EP | 0684012 A2 | 11/1995 | |
| EP | 0727239 A2 | 8/1996 | |
| EP | 0782836 A1 | 7/1997 | |
| EP | 1230899 A1 | 8/2002 | |
| EP | 1674040 A2 | 6/2006 | |
| EP | 1980288 A1 | 10/2008 | |
| EP | 2005912 A2 | 12/2008 | |
| EP | 2537487 A1 | 12/2012 | |
| EP | 2641570 A1 | 9/2013 | |
| EP | 2702965 A1 | 3/2014 | |
| EP | 2740419 A1 | 6/2014 | |
| EP | 3009103 A1 | 4/2016 | |
| FR | 2705556 A1 | 12/1994 | |
| FR | 2768324 A1 | 3/1999 | |
| FR | 2903292 A1 * | 1/2008 | ..... A61B 17/320016 |
| GB | 1598111 A | 9/1981 | |
| GB | 2151142 A | 7/1985 | |
| JP | 09-253030 A | 9/1997 | |
| JP | 11-089937 A | 4/1999 | |
| JP | 2000-283130 A | 10/2000 | |
| JP | 2001517529 A * | 10/2001 | ........... A61B 18/149 |
| JP | 2006-528911 A | 12/2006 | |
| JP | 2013-516244 A | 5/2013 | |
| JP | 2014-523274 A | 9/2014 | |
| JP | 2015-502548 A | 1/2015 | |
| JP | 2018030008 A * | 3/2018 | ......... A61B 1/00087 |
| WO | 81/00668 A1 | 3/1981 | |
| WO | 91/01689 A1 | 2/1991 | |
| WO | 91/18881 A1 | 12/1991 | |
| WO | 92/12690 A1 | 8/1992 | |
| WO | 94/18881 A1 | 9/1994 | |
| WO | 94/18893 A1 | 9/1994 | |
| WO | 95/08292 A1 | 3/1995 | |
| WO | 95/11620 A2 | 5/1995 | |
| WO | 95/15715 A1 | 6/1995 | |
| WO | 96/14032 A1 | 5/1996 | |
| WO | 96/20655 A1 | 7/1996 | |

(56) References Cited

FOREIGN PATENT DOCUMENTS

| | | | |
|---|---|---|---|
| WO | 96/22735 | A1 | 8/1996 |
| WO | 96/30072 | A1 | 10/1996 |
| WO | 97/18746 | A2 | 5/1997 |
| WO | 97/25927 | A1 | 7/1997 |
| WO | 97/26034 | A1 | 7/1997 |
| WO | 97/38748 | A2 | 10/1997 |
| WO | 97/39688 | A2 | 10/1997 |
| WO | 97/48436 | A2 | 12/1997 |
| WO | 98/07375 | A1 | 2/1998 |
| WO | 98/24372 | A1 | 6/1998 |
| WO | 98/30153 | A1 | 7/1998 |
| WO | 98/32382 | A1 | 7/1998 |
| WO | 98/35638 | A1 | 8/1998 |
| WO | 99/00059 | A1 | 1/1999 |
| WO | 99/01377 | A1 | 1/1999 |
| WO | 99/07295 | A1 | 2/1999 |
| WO | 99/07354 | A2 | 2/1999 |
| WO | 99/13777 | A1 | 3/1999 |
| WO | 99/44524 | A2 | 9/1999 |
| WO | 99/66967 | A1 | 12/1999 |
| WO | 00/02489 | A1 | 1/2000 |
| WO | 00/03651 | A1 | 1/2000 |
| WO | 00/03759 | A2 | 1/2000 |
| WO | 00/12168 | A1 | 3/2000 |
| WO | 00/44313 | A1 | 8/2000 |
| WO | 00/59382 | A1 | 10/2000 |
| WO | 00/60995 | A2 | 10/2000 |
| WO | 01/00111 | A1 | 1/2001 |
| WO | 01/00114 | A1 | 1/2001 |
| WO | 01/03651 | A2 | 1/2001 |
| WO | 01/26557 | A1 | 4/2001 |
| WO | 01/26586 | A1 | 4/2001 |
| WO | 01/26587 | A1 | 4/2001 |
| WO | 01/26588 | A2 | 4/2001 |
| WO | 01/26703 | A1 | 4/2001 |
| WO | 01/28432 | A1 | 4/2001 |
| WO | 01/28455 | A1 | 4/2001 |
| WO | 01/47438 | A1 | 7/2001 |
| WO | 01/49213 | A2 | 7/2001 |
| WO | 01/50985 | A1 | 7/2001 |
| WO | 01/54618 | A1 | 8/2001 |
| WO | 01/56512 | A1 | 8/2001 |
| WO | 01/66001 | A2 | 9/2001 |
| WO | 01/70320 | A1 | 9/2001 |
| WO | 01/89440 | A2 | 11/2001 |
| WO | 01/95831 | A2 | 12/2001 |
| WO | 01/95832 | A2 | 12/2001 |
| WO | 01/97741 | A2 | 12/2001 |
| WO | 02/00099 | A2 | 1/2002 |
| WO | 02/01999 | A2 | 1/2002 |
| WO | 02/03892 | A1 | 1/2002 |
| WO | 02/34167 | A2 | 5/2002 |
| WO | 02/60352 | | 8/2002 |
| WO | 02/62263 | | 8/2002 |
| WO | 02/62270 | | 8/2002 |
| WO | 02/62408 | | 8/2002 |
| WO | 03/01893 | A2 | 1/2003 |
| WO | 03/03930 | | 1/2003 |
| WO | 03/20179 | | 3/2003 |
| WO | 03/28558 | A2 | 4/2003 |
| WO | 03/37171 | | 5/2003 |
| WO | 03/47467 | | 6/2003 |
| WO | 03/49619 | | 6/2003 |
| WO | 03/73910 | | 9/2003 |
| WO | 03/73913 | | 9/2003 |
| WO | 03/82129 | | 10/2003 |
| WO | WO-03088809 A2 * | 10/2003 | ..... A61B 17/320016 |
| WO | 2003/105667 | | 12/2003 |
| WO | 2004/004607 | A1 | 1/2004 |
| WO | 2004/006810 | A1 | 1/2004 |
| WO | 2004/012583 | A2 | 2/2004 |
| WO | 2004/012789 | A2 | 2/2004 |
| WO | 2004/014282 | A2 | 2/2004 |
| WO | 2004/019811 | A2 | 3/2004 |
| WO | 2004/030570 | A2 | 4/2004 |
| WO | 2004/037317 | A2 | 5/2004 |
| WO | 2004/045370 | A2 | 6/2004 |
| WO | 2004/045378 | A2 | 6/2004 |
| WO | 2004/045463 | A2 | 6/2004 |
| WO | 2004/047679 | A1 | 6/2004 |
| WO | 2004/062725 | A1 | 7/2004 |
| WO | 2004/082523 | A2 | 9/2004 |
| WO | 2004/082538 | A2 | 9/2004 |
| WO | 2004/093730 | A2 | 11/2004 |
| WO | 2004/103162 | A2 | 12/2004 |
| WO | 2004/112585 | A2 | 12/2004 |
| WO | 2004/112651 | A2 | 12/2004 |
| WO | 2005/002424 | A2 | 1/2005 |
| WO | 2005/018507 | A2 | 3/2005 |
| WO | 2005/027797 | A1 | 3/2005 |
| WO | 2005/032421 | A2 | 4/2005 |
| WO | 2005/062931 | A2 | 7/2005 |
| WO | 2005/112792 | A2 | 12/2005 |
| WO | 2006/037073 | A2 | 4/2006 |
| WO | 2006/105008 | A1 | 10/2006 |
| WO | 2006/105009 | A1 | 10/2006 |
| WO | 2006/113906 | A1 | 10/2006 |
| WO | 2006/115875 | A2 | 11/2006 |
| WO | 2006/115876 | A2 | 11/2006 |
| WO | 2007/136829 | A1 | 11/2007 |
| WO | 2008/103722 | A2 | 8/2008 |
| WO | 2010/024801 | A1 | 3/2010 |
| WO | 2010/121076 | A2 | 10/2010 |
| WO | 2012/020521 | A1 | 2/2012 |
| WO | 2013/049734 | A1 | 4/2013 |
| WO | 2013/103934 | A1 | 7/2013 |
| WO | 2014/064694 | A2 | 5/2014 |
| WO | 2014/121280 | A2 | 8/2014 |
| WO | 2016/022797 | A1 | 2/2016 |
| WO | 2016/144708 | A1 | 9/2016 |
| WO | 2016/150806 | A1 | 9/2016 |
| WO | 2017/223073 | A1 | 12/2017 |
| WO | 2018/009718 | A1 | 1/2018 |
| WO | 2018/106482 | A1 | 6/2018 |
| WO | 2018/236766 | A1 | 12/2018 |
| WO | 2019/040943 | A1 | 2/2019 |
| WO | 2019/195336 | A1 | 10/2019 |

OTHER PUBLICATIONS

Park et al, Clinical Use of Blade Atrial Septostomy, Circulation, 1978, pp. 600-608, vol. 58.

Patel et al., #57 Epicardial Atrial Defibrillation: Novel Treatment of Postoperative Atrial Fibrillation, 2003 STS Presentation, [Abstract Only].

Privitera et al., "Alfieri Mitral Valve Repair: Clinical Outcome and Pathology," Circulation, 106:e173-e174 (2002).

Redaelli et al., "A Computational Study of the Hemodynamics After 'Edge-To-Edge' Mitral Valve Repair," Journal of Biomechanical Engineering, 123:565-570 (2001).

Reul et al., "Mitral Valve Reconstruction for Mitral Insufficiency," Progress in Cardiovascular Diseases, XXXIX(6):567-599 (1997).

Ricchi et al, Linear Segmental Annuloplasty for Mitral Valve Repair, Ann. Thorac. Surg., Jan. 7, 1997, pp. 1805-1806, vol. 63.

Robicsek et al., #60 The Bicuspid Aortic Valve: How Does It Function? Why Does It Fail? 2003 STS Presentation, [Abstract Only].

Rose et al., "Late MitraClip Failure: Removal Technique for Leaflet-Sparing Mitral Valve Repair", Journal of Cardiac Surgery, (Jul. 4, 2012), XP055047339, DOI: 10.1111/j. 1540-8191.2012.01483.x [retrieved on Dec. 11, 2012].

Supplemental European Search Report of EP Application No. 02746781, dated May 13, 2008, 3 pages total.

Supplementary European Search Report issued in European Application No. 05753261.6 dated Jun. 9, 2011, 3 pages total.

Tager et al, Long-Term Follow-Up of Rheumatic Patients Undergoing Left-Sided Valve Replacement With Tricuspid Annuloplasty—Validity of Preoperative Echocardiographic Criteria in the Decision to Perform Tricuspid Annuloplasty, Am. J. Cardiol., Apr. 15, 1998, pp. 1013-1016, vol. 81.

(56) References Cited

OTHER PUBLICATIONS

Takizawa H et al: Development of a microfine active bending catheter equipped with MIF tactile sensors, Micro Electro Mechanical Systems, 1999. MEMS '99. Twelfth IEEE Interna Tional Conference on Orlando, FL, USA Jan. 17-21, 1999, Piscataway, NJ, USA, IEEE, US, Jan. 17, 1999 (Jan. 17, 1999), pp. 412-417, XP010321677, ISBN: 978-0-7803-5194-3 figures 1-3.
Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).
Tibayan et al., #59 Annular Geometric Remodeling in Chronic Ischemic Mitral Regurgitation, 2003 STS Presentation, [Abstract Only].
Timek et al., "Edge-to-edge mitral repair: gradients and three-dimensional annular dynamics in vivo during inotropic stimulation," Eur J. of Cardiothoracic Surg., 19:431-437 (2001).
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
Totaro, "Mitral valve repair for isolated prolapse of the anterior leaflet: an 11-year follow-up," European Journal of Cardio-thoracic Surgery, 15:119-126 (1999).
U.S. Provisional Application filed Jul. 6, 2016, by Khairkhahan., U.S. Appl. No. 62/359,121.
U.S. Provisional Application filed Nov. 7, 2016, by Khairkhahan., U.S. Appl. No. 62/418,571.
U.S. Provisional Application filed Oct. 22, 2018, by Dale et al., U.S. Appl. No. 62/748,947.
Uchida et al, Percutaneous Cardiomyotomy and Valvulotomy with Angioscopic Guidance, Am. Heart J., Apr. 1991, pp. 1221-1224, vol. 121.
Umana et al, 'Bow-Tie' Mitral Valve Repair: An Adjuvant Technique for Ischemic Mitral Regurgitation, Ann. Thorac. Surg., May 12, 1998, pp. 1640-1646, vol. 66.
Umana et al., "'Bow-tie' Mitral Valve Repair Successfully Addresses Subvalvular Dysfunction in Ischemic Mitral Regurgitation," Surgical Forum, XLVIII:279-280 (1997).
U.S. Appl. No. 14/216,813, filed Mar. 17, 2014, Hernandez.
Votta et al., "3-D Computational Analysis of the Stress Distribution on the Leaflets after Edge-to-Edge Repair of Mitral Regurgitation," Journal of Heart Valve Disease, 11:810-822 (2002).
Kruger et al., "P73—Edge to Edge Technique in Complex Mitral Valve Repair," Thorac Cardiovasc Surg., 48(Suppl. 1):106 (2000).
Langer et al., "Posterier mitral leaflet extensions: An adjunctive repair option for ischemic mitral regurgitation?" J Thorac Cardiovasc Surg, 131:868-877 (2006).
Lorusso et al., "The double-orifice technique for mitral valve reconstruction: predictors of postoperative outcome," Eur J. Cardiothorac Surg, 20:583-589 (2001).
Maisano et al, The Edge-to-edge Technique: A Simplified Method to Correct Mitral Insufficiency, Eur. J. Cardiothorac. Surg., Jan. 14, 1998, pp. 240-246, vol. 13.
Maisano et al, The future of transcatheter mitral valve interventions: competitive or complementary role of repair vs. replacement? Eur Heart J. Jul. 7, 2015; 36(26):1651-1659.
Maisano et al., "The double orifice repair for Barlow Disease: a simple solution for a complex repair," Supplement I Circulation, (Nov. 1999); 100(18):1-94.
Maisano et al., "The double orifice technique as a standardized approach to treat mitral regurgitation due to severe myxomatous disease: surgical technique," European Journal of Cardio-thoracic Surgery, 17:201-205 (2000).
Maisano et al., "The Future of Transcatheter Mitral Valve Interventions: Competitive or Complementary Role of Repair vs. Replacement? ", Eur Heart J.36(26): 1651-1659 ( Jul. 7, 2015 ).
Maisano et al., "The hemodynamic effects of double-orifice valve repair for mitral regurgitation: a 3D computational model," European Journal of Cardio-thoracic Surgery, 15:419-425 (1999).
Maisano et al., "Valve repair for traumatic tricuspid regurgitation," Eur. J. Cardio-thorac Surg, (1996) 10:867-873.
Mantovani et al., "Edge-to-edge Repair of Congenital Familiar Tricuspid Regurgitation: Case Report," J. Heart Valve Dis., 9:641-643 (2000).
McCarthy et al, "Tricuspid Valve Repair With the Cosgrove-Edwards Annuloplasty System", Ann. Thorac. Surg., 64:267-8 ( Jan. 16, 1997).
McCarthy et al., "Partial left ventriculectomy and mitral valve repair for end-stage congestive heart failure," European Journal of Cardio-thoracic Surgery, 13:337-343 (1998).
McCarthy et al., "Tricuspid Valve Repair With the Cosgrove-Edwards Annuloplasty System", Ann. Throac Surg. 64:267-8 (Jan. 16, 1997).
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37: 263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. 1):1-1-29-35 (2001).
Noera et al., "Tricuspid Valve Incompetence Caused by Nonpenetrating Thoracic Trauma", Annals of Thoracic Surgery, 51:320-322 (1991).
Notice of Allowance received for U.S. Appl. No. 14/216,787, filed Nov. 7, 2016.
Notice of Allowance received for U.S. Appl. No. 14/216,787, mailed on Nov. 7, 2016.
Notice of Allowance received for U.S. Appl. No. 14/577,852, filed Apr. 25, 2018.
Notice of Allowance received for U.S. Appl. No. 14/577,852, mailed on Apr. 25, 2018.
Notice of Allowance received for U.S. Appl. No. 15/642,245, mailed on Jan. 29, 2020.
Notice of Allowance received for U.S. Appl. No. 15/642,245, mailed on Mar. 27, 2020.
Notice of Allowance received for U.S. Appl. No. 15/642,245, mailed on Nov. 6, 2019.
Notice of Allowance received for U.S. Appl. No. 15/423,060, mailed on Jan. 27, 2020.
Office Action received for U.S. Appl. No. 14/216,787, filed Apr. 8, 2016.
Office Action received for U.S. Appl. No. 14/216,787, mailed on Apr. 8, 2016.
Office Action received for U.S. Appl. No. 14/216,813, filed Apr. 6, 2018.
Office Action received for U.S. Appl. No. 14/216,813, filed Dec. 15, 2017.
Office Action received for U.S. Appl. No. 14/216,813, filed Mar. 9, 2017.
Office Action received for U.S. Appl. No. 14/216,813, mailed on Apr. 6, 2018.
Office Action received for U.S. Appl. No. 14/216,813, mailed on Dec. 15, 2017.
Office Action received for U.S. Appl. No. 14/216,813, mailed on Mar. 9, 2017.
Office Action received for U.S. Appl. No. 14/577,852, filed May 16, 2017.
Office Action received for U.S. Appl. No. 14/577,852, filed Oct. 20, 2016.
Office Action received for U.S. Appl. No. 14/577,852, filed Sep. 7, 2017.
Office Action received for U.S. Appl. No. 14/577,852, mailed on May 16, 2017.
Office Action received for U.S. Appl. No. 14/577,852, mailed on Oct. 20, 2016.
Office Action received for U.S. Appl. No. 14/577,852, mailed on Sep. 7, 2017.

(56) References Cited

OTHER PUBLICATIONS

Office Action received for U.S. Appl. No. 15/423,060, mailed on Apr. 25, 2019.
Office Action received for U.S. Appl. No. 15/423,060, mailed on Aug. 19, 2019.
Office Action received for U.S. Appl. No. 15/423,060, mailed on Oct. 28, 2019.
Office Action received for U.S. Appl. No. 15/642,245, mailed on Aug. 9, 2019.
Office Action received for U.S. Appl. No. 15/724,545, filed Dec. 27, 2019.
Office Action received for U.S. Appl. No. 15/724,545, mailed on Dec. 27, 2019.
Office Action received for U.S. Appl. No. 15/724,545, mailed on May 1, 2020.
Osawa et al., "Partial Left Ventriculectomy in a 3-Year Old Boy with Dilated Cardiomyopathy," Japanese Journal of Thoracic and Cardiovascular Surg, 48:590-593 (2000).
Abe et al, "De Vega's Annuloplasty for Acquired Tricuspid Disease: Early and Late Results in 110 Patients", Ann. Thorac. Surg., pp. 670-676, vol. 48 (Jan. 1989).
Abe et al., "Updated in 1996—De Vega's Annuloplasty for Acquired Tricuspid Disease: Early and Late Results in 110 Patients", Ann. Thorac. Surg., pp. 1876-1877, vol. 62 (1996).
Agricola et al., "Mitral Valve Reserve in Double Orifice Technique: an Exercise Echocardiographic Study," Journal of Heart Valve Disease, 11(5):637-643 (2002).
Alfieri et al., "An Effective Technique to Correct Anterior Mitral Leaflet Prolapse," J. Card Surg., 14:468-470 (1999).
Alfieri et al., "Novel Suture Device for Beating Heart Mitral Leaflet Approximation," Annals of Thoracic Surgery, 74:1488-1493 (2002).
Alfieri et al., "The double orifice technique in mitral valve repair: a simple solution for complex problems," Journal of Thoracic and Cardiovascular Surgery, 122:674-681 (2001).
Alfieri et al., "The Edge to Edge Technique," The European Association For Cardio-Thoracic Surgery, 14th Annual Meeting, Frankfurt/ Germany, Oct. 7-11, 2000, Post Graduate Courses, Book of Proceedings.
Alfieri, "The Edge-to-Edge Repair of the Mitral Valve," [Abstract] 6th Annual New Era Cardiac Care: Innovation & Technology, Heart Surgery Forum, (Jan. 2003) pp. 103.
Ali Khan et al, Blade Atrial Septostomy: Experience with the First 50 Procedures, Cathet. Cardiovasc. Diagn., Aug. 1991, pp. 257-262, vol. 23.
Alvarez et al, Repairing the Degenerative Mitral Valve: Ten to Fifteen-year Follow-up, Journal Thoracic of Cardiovascular Surgery, Aug. 1996, pp. 238-247, vol. 112, No. 2.
Arisi et al., "Mitral Valve Repair with Alfieri Technique in Mitral Regurgitation of Diverse Etiology: Early Echocardiographic Results," Circulation Supplement II, 104(17):3240 (2001).
Bach et al, Early Improvement in Congestive Heart Failure After Correction of Secondary Mitral Regurgitation in End-stage Cardiomyopathy, American Heart Journal, Jun. 1995, pp. 1165-1170, vol. 129, No. 6.
Bach et al., Improvement Following Correction of Secondary Mitral Regurgitation in End-stage Cardiomyopathy With Mitral Annuloplasty, Am. J. Cardiol., Oct. 15, 1996, pp. 966-969, vol. 78.
Bailey, "Mitral Regurgitation" in Surgery of the Heart, Chapter 20, pp. 686-737 (1955).
Bernal et al., "The Valve Racket: a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia, #58 Edge-to-edge mitral repair: a versatile mitral repair technique, 2003 STS Presentation, [Abstract Only], 2004.
Bolling et al, Surgery for Acquired Heart Disease: Early Outcome of Mitral Valve Reconstruction in Patients with End-stage Cardiomyopathy, Journal of Thoracic and Cariovascular Surgery, Apr. 1995, pp. 676-683, vol. 109, No. 4.
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Chinese Office Action issued in Chinese Application No. 200980158707.2 dated Sep. 9, 2013.
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Dang N C et al., "Surgical Revision After Percutaneous Mitral Valve Repair with a Clip: Initial Multicenter Experience", The Annals of Thracic Surgery, Elsevier, United States, vol. 80, No. 6, pp. 2338-2342, (Dec. 1, 2005), XP027732951, ISSN:0003-4975 [retrieved on Dec. 1, 2005].
Dec et al, Idiopathic Dilated Cardiomyopathy, The New England Journal of Medicine, Dec. 8, 1994, pp. 1564-1575, vol. 331, No. 23.
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6):1141-1146 (2002).
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).
Feldman, et al. Randomized Comparison of Percutaneous Repair and Surgery for Mitral Regurgitation: 5-Year Results of Everest II. J Am Coll Cardiol. Dec. 29, 2015;66(25):2844-2854.
Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).
Frazier et al., #62 Early Clinical Experience with an Implantable, Intracardiac Circulatory Support Device: Operative Considerations and Physiologic Implications, 2003 STS Presentation, 1 page total. [Abstract Only].
Fucci et al., Improved Results with Mitral Valve Repair Using New Surgical Techniques, Eur. J. Cardiothorac. Surg., Nov. 1995, pp. 621-627, vol. 9.
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular vol. Reduction and Reconstruction is Ischemic Cardiomyopathy," Journal of Cardiac Surgery, 14:199-210 (1999).
Gateliene, "Early and postoperative results results of metal and tricuspid valve insufficiency surgical treatment using edge-to-edge central coaptation procedure," (Oct. 2002) 38 (Suppl 2):172 175.
Gatti et al., "The edge to edge technique as a trick to rescue an imperfect mitral valve repair," Eur. J. Cardiothorac Surg, 22:817-820 (2002).
Gundry, "Facile mitral valve repair utilizing leaflet edge approximation: midterm results of the Alfieri figure of eight repair," Presented at the Meeting of the Western Thoracic Surgical Association, (1999).
Gupta et al., #61 Influence of Older Donor Grafts on Heart Transplant Survival: Lack of Recipient Effects, 2003 STS Presentation, [Abstract Only].
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).

(56) References Cited

OTHER PUBLICATIONS

Izzat et al., "Early Experience with Partial Left Ventriculectomy in the Asia-Pacific Region," Annuals of Thoracic Surgery, 67:1703-1707 (1999).
Kallner et al., "Transaortic Approach for the Alfieri Stitch," Ann Thorac Surg, 71:378-380 (2001).
Kameda et al, Annuloplasty for Severe Mitral Regurgitation Due to Dilated Cardiomyopathy, Ann. Thorac. Surg., 1996, pp. 1829-1832, vol. 61.
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Khan et al., "Blade Atrial Septostomy; Experience with the First 50 Procedures", Catheterization and Cardiovascular Diagnosis, 23:257-262 (1991).
Kherani et al., "The Edge-To-Edge Mitral Valve Repair: The Columbia Presbyterian Experience," Ann. Thorac. Surg., 78:73-76 (2004).
Kron et al., "Surgical Relocation of the Posterior Papillary Muscle in Chronic Ischemic Mitral Regurgitation," Annals. Of Thoracic Surgery, 74:600-601 (2002).

\* cited by examiner

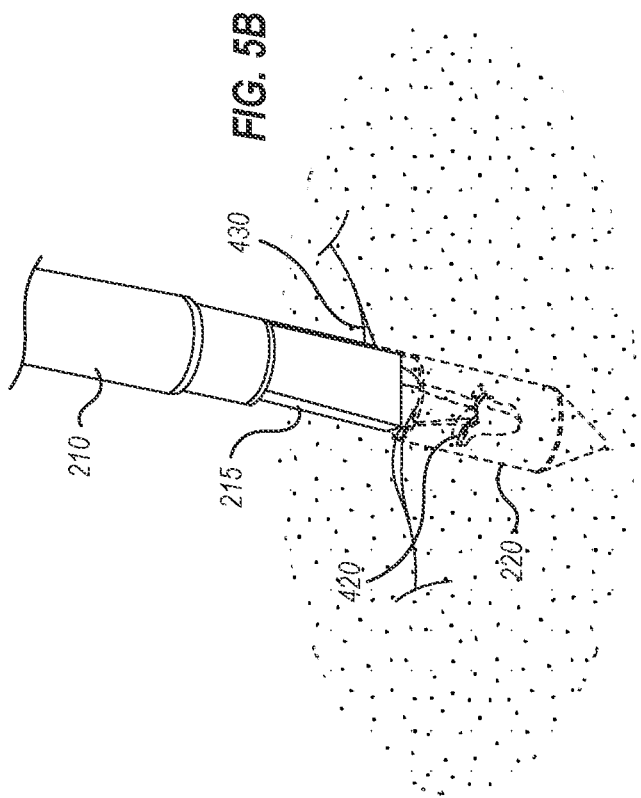
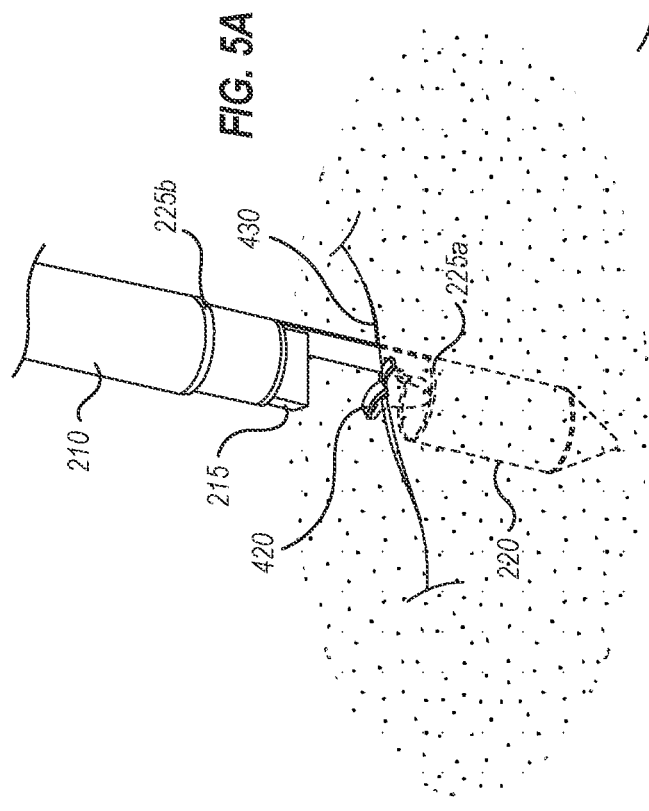
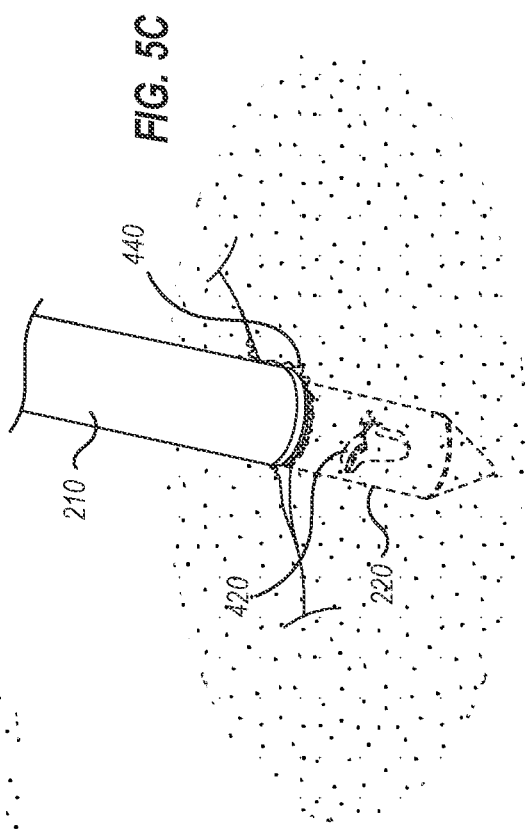

CLIP REMOVAL SYSTEMS AND METHODS

CROSS-REFERENCE TO RELATED APPLICATIONS

This application claims priority to U.S. Provisional Patent Application No. 63/020,673, filed May 6, 2020, the entire contents of which are incorporated by reference herein.

BACKGROUND

The mitral valve controls blood flow from the left atrium to the left ventricle of the heart, preventing blood from flowing backwards from the left ventricle into the left atrium so that it is instead forced through the aortic valve for delivery of oxygenated blood throughout the body. A properly functioning mitral valve opens and closes to enable blood flow in one direction. However, in some circumstances the mitral valve is unable to close properly, allowing blood to regurgitate back into the atrium.

Mitral valve regurgitation has several causes. Functional mitral valve regurgitation is characterized by structurally normal mitral valve leaflets that are nevertheless unable to properly coapt with one another to close properly due to other structural deformations of surrounding heart structures. Other causes of mitral valve regurgitation are related to defects of the mitral valve leaflets, mitral valve annulus, or other mitral valve tissues.

The most common treatments for mitral valve regurgitation rely on valve replacement or repair including leaflet and annulus remodeling, the latter generally referred to as valve annuloplasty. One technique for mitral valve repair which relies on suturing adjacent segments of the opposed valve leaflets together is referred to as the "bowtie" or "edge-to-edge" technique. While all these techniques can be effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity. In some patients, a fixation device can be installed into the heart using minimally invasive techniques. The fixation device can hold the adjacent segments of the opposed valve leaflets together and may reduce mitral valve regurgitation. One such device used to clip the anterior and posterior leaflets of the mitral valve together is the MitraClip® fixation device, sold by Abbott Vascular, Santa Clara, California, USA.

However, sometimes after a fixation device is installed, undesirable mitral valve regurgitation can still exist, or can arise again. For these sub-optimally treated patients, the presence of a fixation device in their mitral valves may obstruct additional procedures such as transcatheter mitral valve replacement. These patients may also be considered too frail to tolerate open-heart surgery, so they are left with no viable options to further improve the function of their mitral valve.

Accordingly, it would be desirable to provide alternative and additional methods, devices, and systems for removing or disabling fixation devices that are already installed. The methods, devices, and systems may be useful for repair of tissues in the body other than heart valves. At least some of these objectives will be met by the inventions described herein.

BRIEF SUMMARY

The present disclosure is directed to systems, methods, and device configured to detach an interventional implant from a cardiac valve. In one embodiment, a capture mechanism includes a capture hypotube having a container portion disposed therein, the container portion being configured to receive and house the interventional implant. The capture mechanism also includes a cutting arm axially translatable relative to the capture hypotube. A first cutting element is disposed at an edge of the capture hypotube, and a second cutting element disposed at an edge of the cutting arm and oriented to face the first cutting element. Axial translation of the cutting arm relative to the capture hypotube brings the first cutting element into contact with the second cutting element to thereby cut cardiac tissue and detach the interventional implant from the cardiac valve.

An embodiment of a system for detaching an interventional implant from a cardiac valve includes a guide catheter having a proximal end and a distal end, wherein the distal end of the guide catheter is steerable to a position near a cardiac valve, and a capture mechanism. The capture mechanism is routable through the guide catheter and configured to extend beyond the distal end of the guide catheter. The capture mechanism is configured to enable capture of the interventional implant and cutting of cardiac tissue to which it is attached to enable detachment of the interventional implant.

An embodiment of a method for detaching an interventional implant from a cardiac valve includes the steps of positioning a guide catheter such that the distal end of the guide catheter is positioned near a targeted cardiac valve, extending a capture mechanism beyond the distal end of the guide catheter, receiving the interventional implant into a container portion of the capture mechanism, and actuating a cutting arm of the capture mechanism to cut cardiac tissue and thereby detach the interventional implant from the cardiac tissue. The interventional implant may be a fixation device attached to adjacent leaflets of the cardiac valve.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 5A-5C illustrate detailed views of the capture mechanism at the mitral valve to illustrate capture of the interventional fixation device and cutting of surrounding leaflet tissue to free the captured fixation device.

DETAILED DESCRIPTION

Introduction

Embodiments described herein are configured to effectively capture an interventional implant positioned at a targeted cardiac valve, and to free the implant from surrounding leaflet tissue so that the implant may be removed from the cardiac valve. Removal of such implants (e.g., fixation devices) can beneficially enable further interventional procedures at the cardiac valve, such as placement and implantation of a prosthetic replacement valve.

Figure 1:
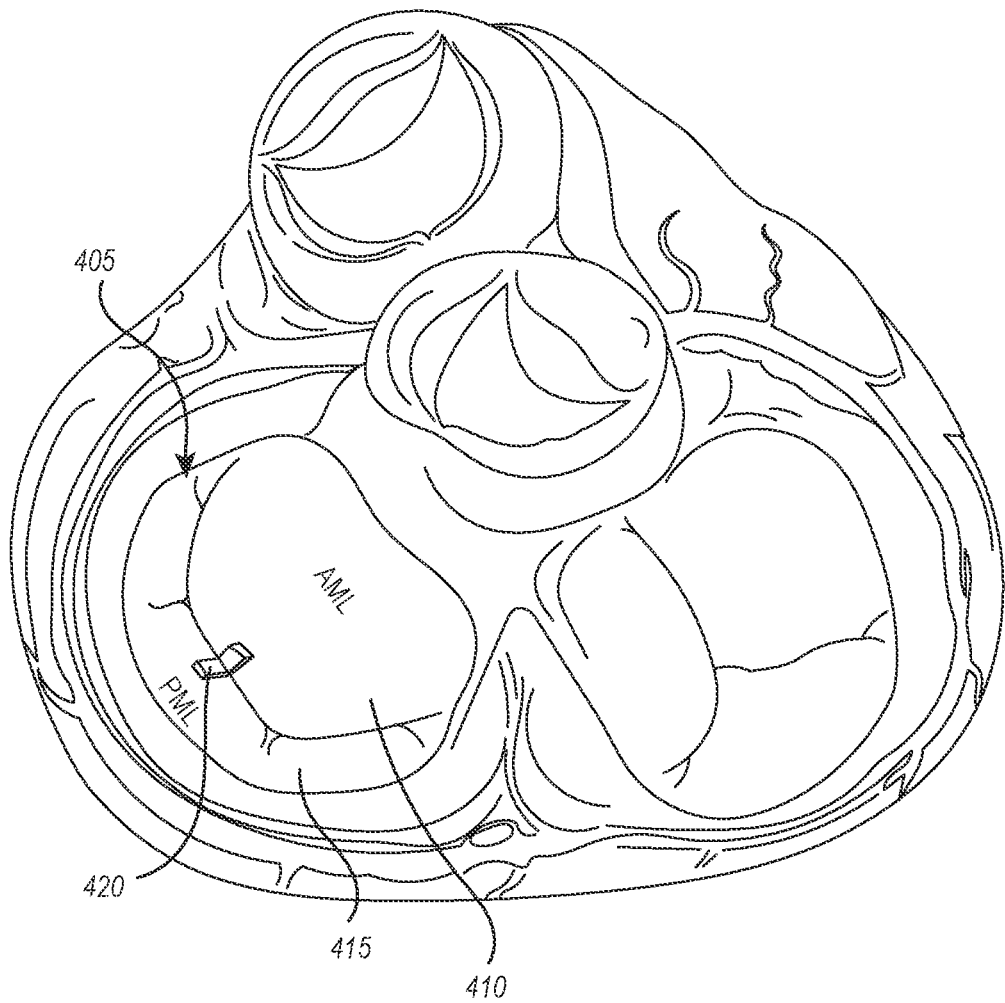
FIG. 1 illustrates a cross-sectional view of a human heart from a superior perspective, showing the mitral valve with an implanted clip fixation device for holding anterior and posterior leaflets of the mitral valve together.

FIG. 1 illustrates a cross-sectional view of a human heart from a superior perspective, showing the mitral valve 405, which includes an anterior leaflet 410 and a posterior leaflet 415. A clip fixation device 420 has been positioned in the mitral valve 405 to clip and hold the leaflets 410 and 415 together at the coapting edges. As explained above, such repair devices are often placed with the intent of reducing mitral valve regurgitation. However, if excessive regurgitation remains following placement of the device 420, and further interventional procedures are necessary or desired, the fixation device 420 may need to be detached from leaflet tissue and/or removed from the mitral valve 405. For example, the fixation device 420 may need to be repositioned or removed prior to the placement of a replacement valve.

Although the examples described herein are provided in the context of capturing a fixation device implanted at a mitral valve, one skilled in the art will appreciate that the embodiments described herein are not necessarily limited to use within the mitral valve 405. In other applications, the targeted cardiac valve could be the tricuspid valve, aortic valve, or pulmonic valve for example. More generally, the embodiments described herein may be utilized in other implementations involving capture and removal of a previously implanted or deployed device from tissue.

In addition, although examples may illustrate routing a guide catheter to the mitral valve via a transfemoral/transseptal or transjugular/transseptal approach, other suitable delivery approaches may be used, including radial or transapical approaches.

Delivery System Overview

Figure 2A:
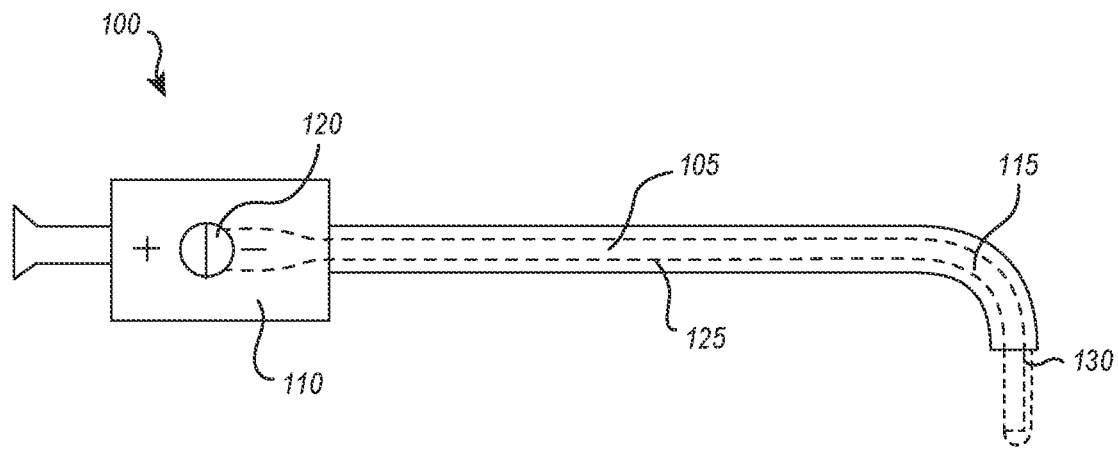
FIG. 2A illustrates an exemplary delivery system that may be utilized for guiding and/or delivering a capture mechanism to a cardiac valve to enable detaching an interventional implant therefrom.

FIG. 2A illustrates an exemplary embodiment of a delivery system 100 that may be utilized for guiding and/or delivering a capture mechanism 130 to a targeted cardiac valve to enable detaching an interventional implant from the cardiac valve. In at least one embodiment, the delivery system 100 includes a guide catheter 105 having a proximal end and a distal end 115. The delivery system may comprise a handle 110 positioned on the proximal end of the guide catheter 105. The guide catheter 105 may be operatively coupled to the handle 110. The guide catheter 105 may be steerable to enable the guiding and orienting of the guide catheter 105, including the distal end 115 of the guide catheter 105. For example, the handle 110 may include at least one control 120 (e.g., a dial, a switch, a slider, a button, etc.) that can be actuated to control the movement and curvature of the distal end 115 of the guide catheter 105.

As one example of a steering mechanism, the at least one control 120 may be operatively coupled to one or more control lines 125 (e.g., pull wires) extending from the handle 110 through the guide catheter 105 to the distal end 115 of the guide catheter (e.g., through one or more lumens in the guide catheter 105). Actuation of the at least one control 120 may adjust the tensioning of a control line 125 to pull the guide catheter 105 in the corresponding direction.

FIG. 2A shows a pair of control lines 125. Alternatively, a handle 110 may comprise more than one control 120 configured for controlling steering and any number of associated control lines. For example, the delivery system 100 may be configured to provide bending of the guide catheter 105 in multiple planes and/or at multiple bending points along the length of the guide catheter 105.

The control 120 and/or other controls disposed at the handle 110 may also be utilized to control actuation of various components of the capture mechanism 130. As shown, the capture mechanism 130 is configured in size and shape so as to be routable through the guide catheter 105 and extendable beyond the distal end 115 of the guide catheter 105. The capture mechanism 130 may also be retracted back into the guide catheter 105.

Control(s) 120 may control the capture mechanism's 130 extension through and retraction back into the guide catheter 105. Additionally, or alternatively, the control(s) 120 may be configured to provide selective actuation of one or more components of the capture mechanism 130 described further below. The capture mechanism 130 is shown in generic form and therefore represents any of the capture mechanism 130 embodiments described herein.

Figure 2B:
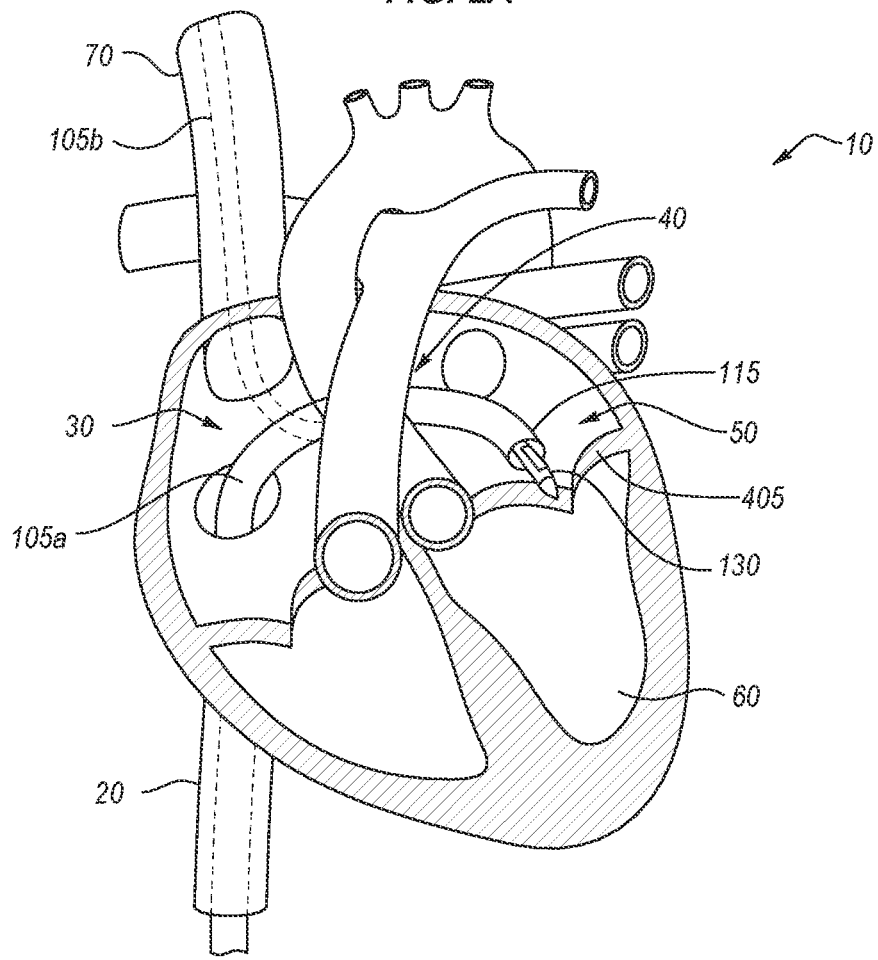
FIG. 2B illustrates a cross-sectional view of a human heart from an anterior perspective showing exemplary approaches for positioning a capture mechanism at a targeted cardiac valve.

FIG. 2B illustrates a cross-sectional view of a patient's heart 10 from an anterior perspective, showing an exemplary approach for delivering the capture mechanism to the targeted mitral valve 405 using the guide catheter 105. In particular, FIG. 2B illustrates a transfemoral approach via guide catheter 105 (shown for this approach as guide catheter 105a), and an alternative transjugular approach via guide catheter 105 (shown for this approach as guide catheter 105b).

In a transfemoral approach, the delivery catheter 105a is inserted into the patient's vasculature at a femoral vein and directed to the inferior vena cava 20. The catheter 105a is passed through the inferior vena cava 20 and into the right atrium 30. In the transjugular approach, the delivery catheter 105b is inserted into the patient's vasculature at a jugular vein and directed to the superior vena cava 70. The catheter 105b is passed through the superior vena cava 70 and into the right atrium 30. Subsequently, in either approach, the distal end 115 of the catheter 105 is pushed across the septum 40 so as to be positioned in the left atrium 50 superior of the mitral valve 405.

As explained further below, the capture mechanism 130 is then directed partially through the mitral valve 405 and partially into the left ventricle 60 so that an interventional implant at the mitral valve 405 can be captured and surrounding leaflet tissue can be cut to free the implant.

Capture Mechanism Details

Figure 3A:
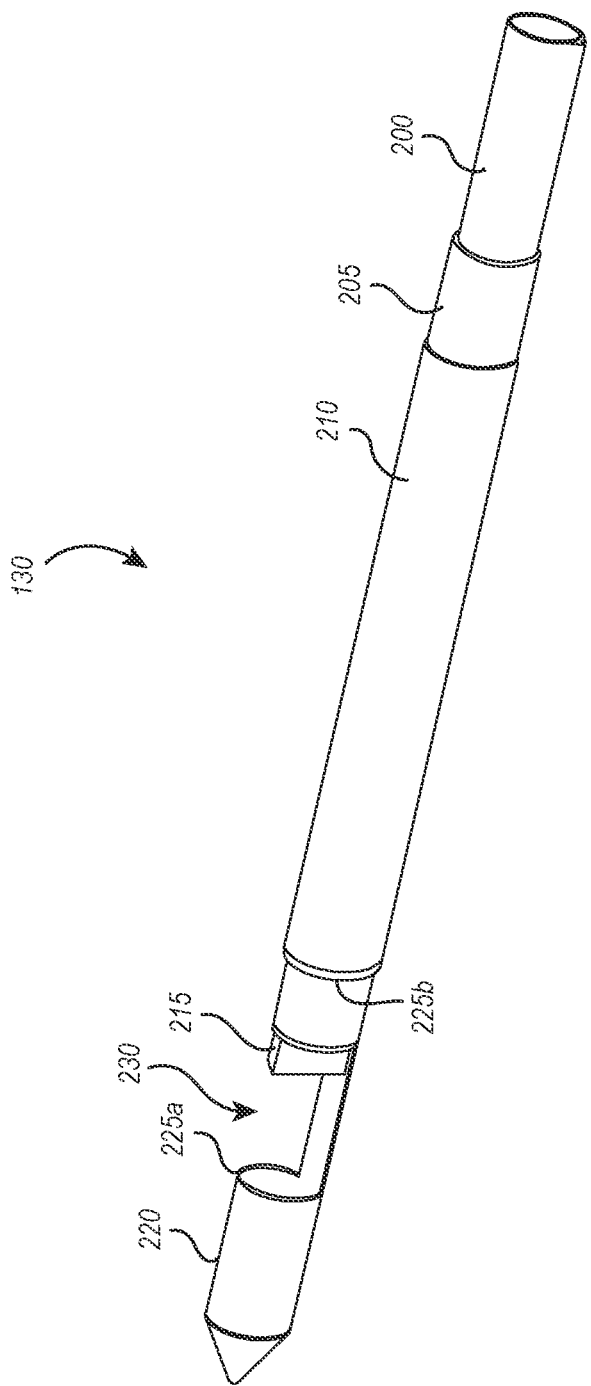
FIGS. 3A-3C are perspective views of an exemplary embodiment of a capture mechanism.
Figure 3B:
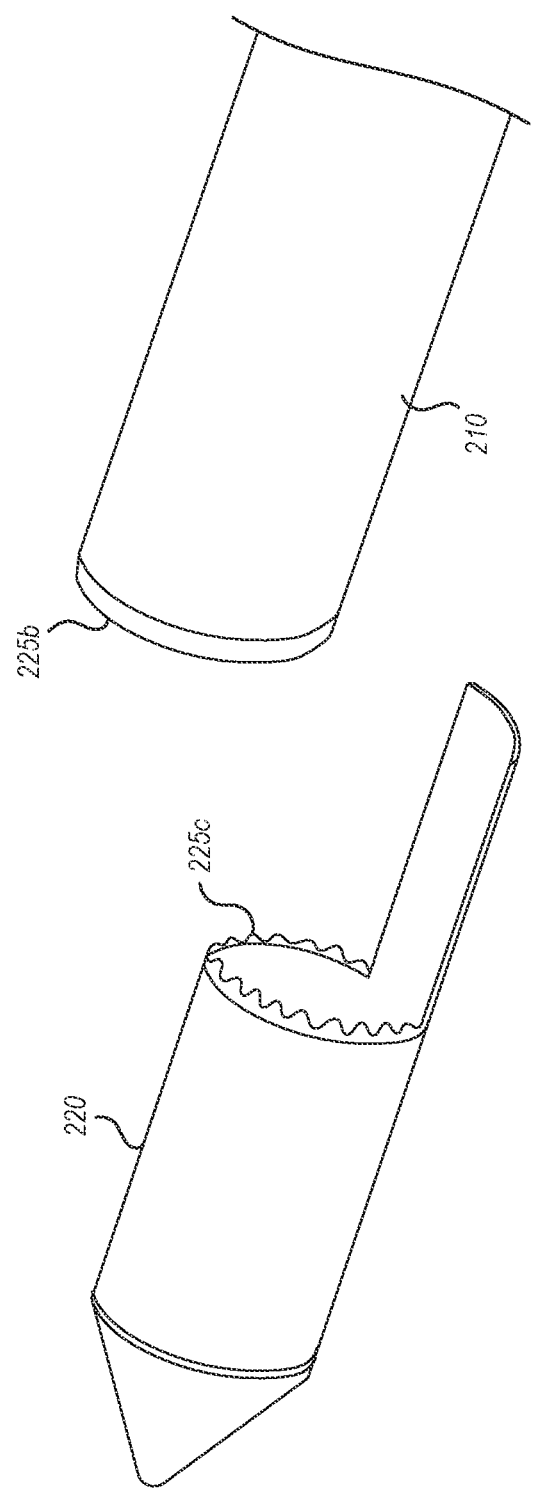
Figure 3C:
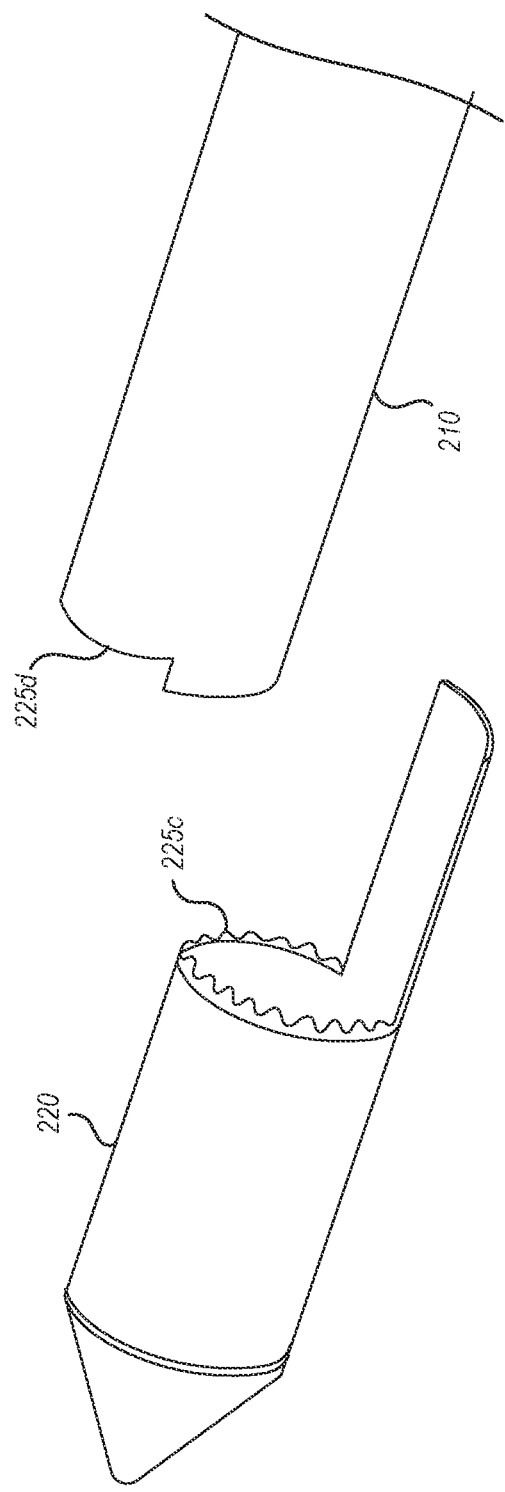

FIGS. 3A-3C are perspective views of an exemplary embodiment of a capture mechanism 130. As shown in FIG. 3A, the capture mechanism 130 may comprise a shaft 200 and a capture hypotube 205. Although in FIG. 2A the capture hypotube 205 is shown outside of the shaft 200, the capture hypotube 205 may alternatively be disposed within the shaft 200 and be configured to retract into the shaft 200. In at least one embodiment, the capture mechanism 130 does not comprise a shaft 200 and the capture hypotube 205 passes directly proximally through the guide catheter 105. The shaft 200 may be configured to move axially relative to the capture hypotube 205 and/or other components of the capture mechanism 130 to control actuation of one or more components of the capture mechanism 130. For example, the shaft 200 may be mechanically coupled to the handle 110 such that operation of one or more controls 120 causes axial movement of the shaft 200 to in turn cause actuation of one or more components of the capture mechanism 130, such as causing corresponding movement of an axial actuator 215.

The capture hypotube 205 may comprise a cutout portion 230 sized to fit an interventional implant targeted for removal. The capture mechanism 130 may further comprise a cutting arm 210 configured to selectively advance relative to the capture hypotube 205 to cover the cutout portion 230 and retract relative to the capture hypotube 205 to uncover the cutout portion 230. The cutting arm 210 may be disposed outside surface of the capture hypotube 205, as shown. Alternatively, the cutting arm 210 may be disposed within the capture hypotube 205. In either configuration, the cutting arm 210 is axially translatable relative to the capture hypotube 205 to provide selective covering and uncovering of the cutout portion 230.

As described in more detail below, the capture hypotube 205 may be positioned adjacent to an interventional implant targeted for removal from a cardiac valve. The interventional implant may be, for example, a fixation device that approximates two adjacent leaflets. Typically, the cutting arm 210 is put in an advanced position to cover the cutout portion 230 during routing of the capture hypotube 205 through the guide catheter 105 and into proper position at the cardiac valve. Then, when the capture hypotube 205 is positioned adjacent to the targeted interventional implant, the cutting arm 210 may be moved to a retracted position so as to uncover the cutout portion 230 of the capture hypotube 205.

The distal end of the capture hypotube 205 may comprise a container portion 220 sized to fit and house the interventional implant after it has passed into the capture hypotube 205 via the cutout portion 230. Although in FIG. 2A the container portion 220 is shown distal to the cutout portion 230, the relative positions of the container portion 220 and the cutout portion 230 may be reversed.

The capture mechanism 130 may comprise an axial actuator 215 configured to advance or retract relative to the capture hypotube 205 and thereby enable advancing/pushing the interventional implant from the cutout portion 230 into the container portion 220 and optionally also retracting/pulling it therefrom. The axial actuator 215 may comprise a pusher, a hook, a block, other structure for manipulating the interventional implant, or combination thereof.

A proximal end of the container portion 220 may comprise a first cutting element 225a. Additionally, or alternatively, a distal end of the cutting arm 210 may comprise a second cutting element 225b. The first and second cutting elements 225a and 225b may be configured to cut tissue surrounding the interventional implant when an interventional implant is positioned within the container portion 220 and the cutting arm 210 is advanced to cover the cutout portion 230 of the capture hypotube 205, and to thereby detach the interventional implant from the surrounding tissue. The cutting arm 210 may also be configured to be rotatable relative to the capture hypotube 205 to actuate and/or assist in cutting tissue.

The first and/or second cutting elements 225a, 225b may comprise sharpened edges that function to cut tissue upon sufficient advancement of the cutting arm 210. Additionally, or alternatively, the first and/or second cutting elements 225a, 225b may comprise electrodes configured to provide radio frequency current energy to tissue. The capture hypotube 205 and/or cutting arm 210 may be coated with an electrically insulating coating material while the first and second cutting mechanisms 225a and 225b remain uncoated. The uncoated edges of the cutting elements 225a and/or 225b may comprise a material with low impedance, such as platinum, iridium, silver, gold, or a combination thereof.

FIGS. 3B and 3C illustrate alternative embodiments of cutting elements that may be utilized with the capture hypotube 205 and/or cutting arm 210. At least one cutting element, shown here as cutting element 225c, may comprise a wavy and/or serrated edge configured to better grip tissue. Additionally, or alternatively, one or more cutting elements may comprise a dual, curved, or spiral-shaped cutting edge, as shown by cutting element 225d of FIG. 3C. The lateral cutting edge of the cutting element 225d may be particularly beneficial for cutting tissue via rotation of the cutting arm 210 relative to the capture hypotube 205. The illustrated cutting elements are merely exemplary and other cutting elements suitable for cutting tissue may additionally or alternatively be utilized. Further, different cutting elements of the capture hypotube 205 and cutting arm 210 may be combined to form other combinations beyond the specific example combinations illustrated in FIGS. 3A-3C.

Capture & Retrieval of an Interventional Implant

Figure 4:
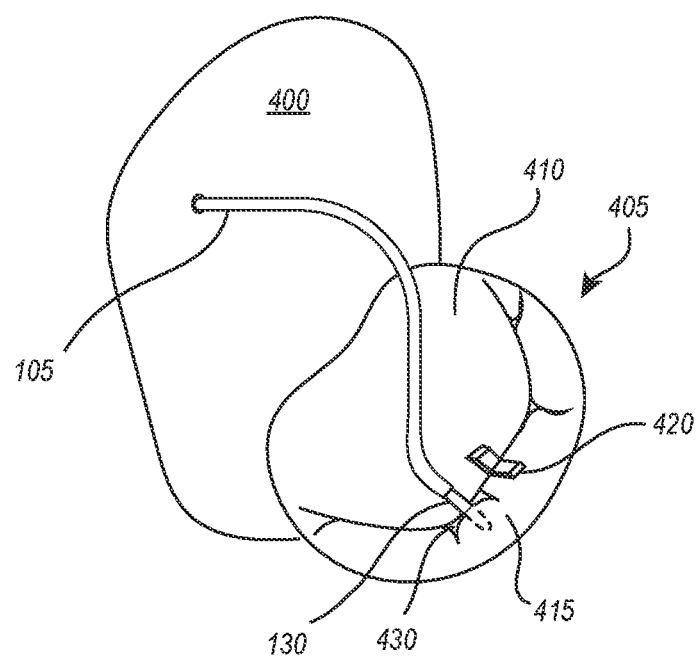
FIG. 4 illustrates delivery of the capture mechanism to the mitral valve and positioning of the capture mechanism relative to an interventional fixation device in preparation for capture and removal of the interventional fixation device.

FIG. 4 illustrates use of the exemplary capture mechanism 130 to capture and retrieve an interventional implant 420 previously implanted at the mitral valve 405. The interventional implant 420 fixes and approximates the leaflets 410 and 415. As shown, the distal end 115 of the guide catheter 105 has been extended through the septum 400. The capture mechanism 130 may be routed through the guide catheter 105 so as to extend through an orifice 430 of the mitral valve 405 and be at least partially disposed on a ventricular side of the valve 405.

FIGS. 5A-5C illustrate an expanded view of the capture mechanism 130 to show exemplary use of the capture mechanism 130 after it has been positioned adjacent to the interventional implant 420. In the example use shown in FIGS. 5A-5C, the distal end of the capture mechanism 130, including the container portion 220 and first cutting element 225a, are positioned on the ventricular side of the mitral valve orifice 430, while the axial actuator 215 and cutting arm 210 are positioned on the atrial side of the mitral valve orifice 430.

As shown in FIG. 5A, the capture mechanism 130 is positioned so that the interventional implant 420 is within the cutout portion 230 and adjacent the container portion 220. The axial actuator 215 may then be actuated to push the interventional implant 420 into the container portion 220, as shown in FIG. 5B. Subsequently, the cutting arm 210 may be advanced relative to the capture hypotube 205 to bring cutting elements 225*a* and 225*b* together against the leaflet tissue. This cuts the leaflet tissue, leaving behind hole 440, and releases the interventional implant 420 from the surrounding mitral valve tissues, as shown in FIG. 5C, so that it can be removed from the patient along with the capture mechanism 130.

Alternative Capture Mechanism Embodiments

Figure 6B:
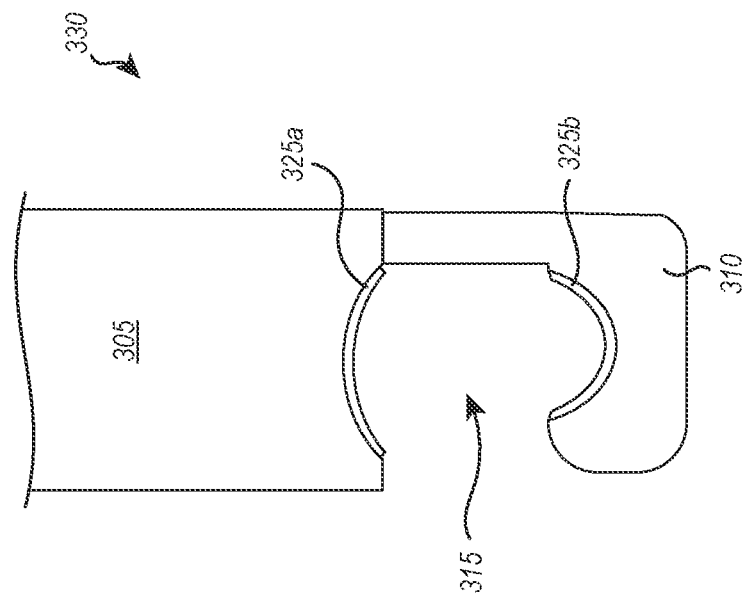
FIGS. 6A and 6B are perspective views of an alternative exemplary embodiment of a capture mechanism according to the present disclosure.
Figure 6A:
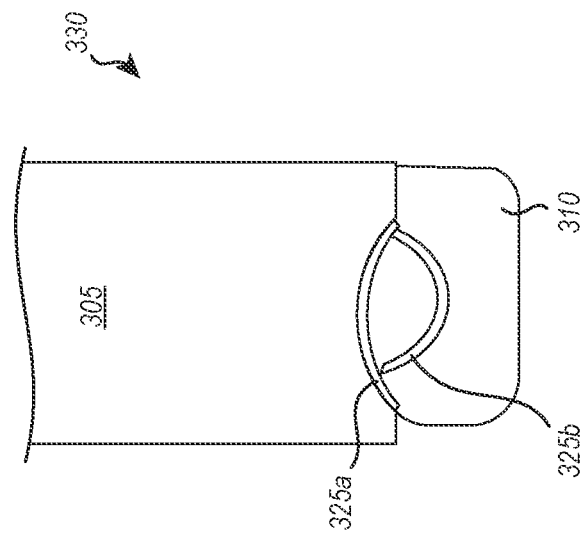

FIGS. 6A and 6B are perspective side views of an alternative exemplary embodiment of a capture mechanism 330. The embodiment illustrated in FIGS. 6A and 6B may be utilized with the delivery system described above and/or in any of the exemplary uses described above for removing an interventional implant from a cardiac valve.

As shown, the capture mechanism 330 may comprise a capture hypotube 305. A distal end of the capture mechanism 330 may comprise cutting arm 310 in the shape of a hook configured to extend from the distal end of the capture hypotube 305, thereby creating a cavity 315 sized to fit the interventional implant, as shown in FIG. 6B. The retractable cutting arm 310 may be extended from the distal end of the capture hypotube 305 when the capture hypotube 305 is at a position adjacent to, and generally aligned with, an interventional implant targeted for removal. The capture mechanism 330 may then be positioned such that the interventional implant is generally within cavity 315. The retractable cutting arm 310 may then be retracted, thereby pulling and securing the interventional implant within a container portion/space of the capture hypotube 305.

As shown, the distal end of the capture hypotube 305 may comprise a first cutting element 325*a*, and an inside surface of the retractable cutting arm 310 may comprise a second cutting element 325*b*. The first and second cutting elements 325*a* and 325*b* may be configured to cut tissue to which the interventional implant is attached when the retractable cutting arm 310 retracts sufficiently to bring the cutting elements 325*a* and 325*b* together, thereby detaching the interventional implant from the surrounding tissue.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

Additional Exemplary Embodiments

Following are some further example embodiments of the invention. These are presented only by way of example and are not intended to limit the scope of the invention in any way.

Embodiment 1. A capture mechanism configured for capturing an interventional implant previously implanted at cardiac valve tissue, the capture mechanism comprising: a capture hypotube having a container portion disposed therein, the container portion being configured to receive and house the interventional implant, a cutting arm axially translatable relative to the capture hypotube; a first cutting element disposed at an edge of the capture hypotube, and a second cutting element disposed at an edge of the cutting arm and oriented to face the first cutting element, wherein axial translation of the cutting arm relative to the capture hypotube brings the first cutting element into contact with the second cutting element to thereby cut cardiac tissue disposed therebetween.

Embodiment 2. The capture mechanism of Embodiment 1, wherein the container portion is adjacent a cutout portion that faces laterally and is configured to receive the interventional implant.

Embodiment 3. The capture mechanism of Embodiment 2, further comprising an axial actuator configured to translate axially relative to the capture hypotube, the axial actuator being configured to extend into the cutout portion to thereby enable the interventional implant to be pushed from the cutout portion toward the adjacent container portion.

Embodiment 4. The capture mechanism of Embodiment 2 or 3, wherein the cutting arm is configured to cover the cutout portion when in an advanced position relative to the capture hypotube and to uncover and expose the cutout portion when in a retracted position relative to the capture hypotube.

Embodiment 5. The capture mechanism of any one of Embodiments 2-4, wherein the container portion is disposed at a distal end of the capture hypotube, and wherein the cutout portion is disposed proximal of the container portion.

Embodiment 6. The capture mechanism of any one of Embodiments 1-5, wherein the first cutting element, the second cutting element, or both comprise sharpened edges.

Embodiment 7. The capture mechanism of any one of Embodiments 1-6, wherein the first cutting element, the second cutting element, or both comprise serrated and/or wavy edges.

Embodiment 8. The capture mechanism of any one of Embodiments 1-7, wherein the first cutting element, the second cutting element, or both comprise a lateral cutting edge.

Embodiment 9. The capture mechanism of any one of Embodiments 1-8, wherein the first cutting element, the second cutting element, or both comprise electrodes conductive to radio frequency energy.

Embodiment 10. The capture mechanism of Embodiment 9, wherein the capture hypotube and the cutting arm are formed from a conductive material and are coated with an insulating coating, except that the first and second cutting elements remain uncoated.

Embodiment 11. The capture mechanism of any one of Embodiments 1-10, wherein the cutting arm is also rotatable relative to the capture hypotube.

Embodiment 12. The capture mechanism of any one of Embodiments 1-11, wherein the cutting arm is formed as a hypotube.

Embodiment 13. The capture mechanism of Embodiment 12, wherein the cutting arm hypotube is disposed outside of the capture hypotube.

Embodiment 14. The capture mechanism of any one of Embodiments 1-13, wherein the first cutting element faces proximally and the second cutting element faces distally.

Embodiment 15. The capture mechanism of any one of Embodiments 1-14, wherein the first cutting element faces distally and the second cutting element faces proximally.

Embodiment 16. The capture mechanism of Embodiment 15, wherein the cutting arm comprises a hook, and wherein the cutting arm is configured to extend beyond a distal end of the capture hypotube to form a cavity between the distal end of the capture hypotube and a proximal side of the hook.

Embodiment 17. The capture mechanism of Embodiment 16, wherein the first cutting element being disposed at the distal end of the capture hypotube and the second cutting element being disposed at the proximal side of the hook.

Embodiment 18. A system for detaching an interventional implant from a cardiac valve, the system comprising: a guide catheter having a proximal end and a distal end, the distal end of the guide catheter being steerable to a position adjacent a cardiac valve; and a capture mechanism as in any one of Embodiments 1-17, routable through the guide catheter and configured to extend beyond the distal end of the guide catheter.

Embodiment 19. The system of Embodiment 18, further comprising a handle coupled to the proximal end of the guide catheter, the handle comprising at least one control operatively connected to the capture mechanism to enable actuation of the cutting arm to thereby provide translation and/or rotation of the cutting arm relative to the capture hypotube.

Embodiment 20. A method of detaching an interventional implant from a cardiac valve within a body, the method comprising: providing a system for detaching an interventional implant from a cardiac valve as in Embodiment 18 or 19, positioning the distal end of the guide catheter near a targeted cardiac valve, the targeted cardiac valve including an interventional implant affixed to cardiac valve tissue, extending the capture mechanism distally beyond the distal end of the guide catheter, capturing the interventional implant within the container portion of the capture hypotube, and actuating the cutting arm to cut cardiac tissue and thereby detach the interventional implant from the cardiac tissue

We claim:

1. A capture mechanism configured for capturing an interventional implant previously implanted at cardiac valve tissue, the capture mechanism comprising:
   a capture hypotube having a container portion disposed distal a cutout portion and adjacent a terminal distal end of the capture hyptotube, the container portion being disposed at a fixed position distal a cutout portion, the container portion being configured to receive and house the interventional implant;
   a cutting arm axially translatable around an outer surface of and rotatable relative to the capture hypotube;
   a first cutting element disposed at an edge of the capture hypotube; and
   a second cutting element disposed at an edge of the cutting arm and oriented to face the first cutting element,
   wherein axial translation of the cutting arm relative to the capture hypotube brings the first cutting element into contact with the second cutting element, thereby causing both first cutting element and second cutting element to cut cardiac tissue disposed therebetween.

2. The capture mechanism of claim 1, wherein the container portion is adjacent the cutout portion that faces laterally and is configured to receive the interventional implant.

3. The capture mechanism of claim 2, further comprising an axial actuator configured to translate axially relative to the capture hypotube, the axial actuator being configured to extend into the cutout portion to thereby enable the interventional implant to be pushed from the cutout portion toward the adjacent container portion.

4. The capture mechanism of claim 2, wherein the cutting arm is configured to cover the cutout portion when in an advanced position relative to the capture hypotube and to uncover and expose the cutout portion when in a retracted position relative to the capture hypotube.

5. The capture mechanism of claim 2, wherein the container portion is disposed at a distal end of the capture hypotube, and wherein the cutout portion is disposed proximal of the container portion.

6. The capture mechanism of claim 1, wherein the first cutting element, the second cutting element, or both comprise sharpened edges.

7. The capture mechanism of claim 1, wherein the first cutting element, the second cutting element, or both comprise serrated and/or wavy edges.

8. The capture mechanism of claim 1, wherein the first cutting element, the second cutting element, or both comprise a lateral cutting edge.

9. The capture mechanism of claim 1, wherein the first cutting element, the second cutting element, or both comprise electrodes conductive to radio frequency energy.

10. The capture mechanism of claim 9, wherein the capture hypotube and the cutting arm are formed from a conductive material and are coated with an insulating coating, except that the first and second cutting elements remain uncoated.

11. The capture mechanism of claim 1, wherein the cutting arm is formed as a hypotube.

12. The capture mechanism of claim 11, wherein the cutting arm hypotube is disposed outside of the capture hypotube.

13. The capture mechanism of claim 1, wherein the first cutting element faces proximally and the second cutting element faces distally.

14. The capture mechanism of claim 1, wherein the first cutting element faces distally and the second cutting element faces proximally.

15. The capture mechanism of claim 14, wherein the cutting arm comprises a hook, and wherein the cutting arm is configured to extend beyond a distal end of the capture hypotube to form a cavity between the distal end of the capture hypotube and a proximal side of the hook.

16. The capture mechanism of claim 15, wherein the first cutting element being disposed at the distal end of the capture hypotube and the second cutting element being disposed at the proximal side of the hook.

17. A system for detaching an interventional implant from a cardiac valve, the system comprising:
   a guide catheter having a proximal end and a distal end, the distal end of the guide catheter being steerable to a position adjacent a cardiac valve; and
   a capture mechanism routable through the guide catheter and configured to extend beyond the distal end of the guide catheter, the capture mechanism comprising:
      a capture hypotube having a container portion distally disposed therein, the container portion being configured to receive and house the interventional implant,
      an axial actuator disposed within the capture hypotube and configured to distally translate axially into a cutout portion to thereby enable the interventional implant to be distally pushed from the cutout portion into the container portion,
      a cutting arm axially translatable around an outer surface of and rotatable relative to the capture hypotube,
      a first cutting element disposed at an edge of the capture hypotube, and
      a second cutting element disposed at an edge of the cutting arm and oriented to face the first cutting element,
      wherein axial translation of the cutting arm relative to the capture hypotube brings the first cutting element into contact with the second cutting element, thereby causing both first cutting element and second cutting element to cut cardiac tissue disposed therebetween.

18. The system of claim 17, further comprising a handle coupled to the proximal end of the guide catheter, the handle comprising at least one control operatively connected to the capture mechanism to enable actuation of the cutting arm to thereby provide translation and/or rotation of the cutting arm relative to the capture hypotube.

19. A method of detaching an interventional implant from a cardiac valve within a body, the method comprising:
providing a system for detaching an interventional implant from a cardiac valve, the system comprising
a guide catheter having a proximal end and a distal end, the distal end of the guide catheter being steerable to a position adjacent a cardiac valve; and
a capture mechanism routable through the guide catheter and configured to extend beyond the distal end of the guide catheter, the capture mechanism comprising
a capture hypotube having a container portion disposed distal a cutout portion and adjacent a terminal distal end of the capture hyptotube, the container portion being disposed at a fixed position distal a cutout portion, the container portion being configured to receive and house the interventional implant,
a cutting arm axially translatable around an outer surface of and rotatable relative to the capture hypotube,
a first cutting element disposed at an edge of the capture hypotube, and
a second cutting element disposed at an edge of the cutting arm and oriented to face the first cutting element,
wherein axial translation of the cutting arm relative to the capture hypotube brings the first cutting element into contact with the second cutting element, thereby causing both first cutting element and second cutting element to cut cardiac tissue disposed therebetween;
positioning the distal end of the guide catheter near a targeted cardiac valve, the targeted cardiac valve including an interventional implant affixed to cardiac valve tissue;
extending the capture mechanism distally beyond the distal end of the guide catheter;
capturing the interventional implant within the container portion of the capture hypotube; and
actuating the cutting arm to cut cardiac tissue and thereby detach the interventional implant from the cardiac tissue.

* * * * *